US007297785B2

(12) United States Patent
Bode et al.

(10) Patent No.: US 7,297,785 B2
(45) Date of Patent: Nov. 20, 2007

(54) **UNIQUE CHROMOSOMAL SEQUENCE OF *BACILLUS ANTHRACIS* AND METHODS OF MAKING AND USING THEREOF INCLUDING REAL-TIME PCR ASSAYS**

(75) Inventors: Elizabeth Bode, Frederick, MD (US); David A. Norwood, Jr., Thurmont, MD (US); William J. Hurtle, Dugway, UT (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 149 days.

(21) Appl. No.: 10/934,488

(22) Filed: Sep. 7, 2004

(65) Prior Publication Data

US 2005/0214787 A1 Sep. 29, 2005

Related U.S. Application Data

(60) Provisional application No. 60/564,639, filed on Apr. 23, 2004, provisional application No. 60/556,045, filed on Mar. 24, 2004.

(51) Int. Cl.
*C07H 21/04* (2006.01)
*C07H 21/02* (2006.01)
*C12Q 1/68* (2006.01)
*C12P 19/34* (2006.01)

(52) U.S. Cl. .................. 536/24.3; 536/23.1; 435/6; 435/91.2

(58) Field of Classification Search .................. None
See application file for complete search history.

(56) References Cited

U.S. PATENT DOCUMENTS

2003/0027169 A1* 2/2003 Zhang et al. .................. 435/6

2004/0241651 A1* 12/2004 Olek et al. .................. 435/6

FOREIGN PATENT DOCUMENTS

WO       WO 0177384 A2 * 10/2001

OTHER PUBLICATIONS

GenBank Locus BZ867717, GI: 29095122, 'CH240_274J15.TV CHORI-240 *Bos taurus* genomic clone CH240_274J15, genomic survey sequence,' Mar. 18, 2003, pp. 1-2.*
BZ867717—SID1 Alignment, pp. 1-2.*
SID 182,309 Alignment and Seq Listing, pp. 1-2.*
Ahern H 'Biochemical, Reagents Kits Offer Scientists Good Return On Investment.' The Scientist 1995, 9(15) pp. 20 and 22.*
Blast 2 Sequences results 'Align SEQ ID No. 1—GI:30257133', pp. 1-2.*
GenBank Locus AE017032, GI: 30257133 '*Bacillus anthracis* str. Ames section 9 of 18 of the complete genome'. Apr. 30, 2003, pp. 1-164.*
AB017032 Sequence alignment.
Read et al. (2003) "The Genome Sequence of *Bacillus anthracis* Ames and Comparison to Closely Related Bacteria" Nature 423:81-86.
ISR PCT/US04/28978.
Written Opinion PCT/US04/28978.

* cited by examiner

*Primary Examiner*—BJ Foreman
*Assistant Examiner*—Stephen Kapushoc
(74) *Attorney, Agent, or Firm*—Elizabeth Arwine

(57) ABSTRACT

Disclosed herein are nucleic acid molecules having sequences that are unique to *Bacillus anthracis* and method of making and using thereof. Also disclosed are kits comprising the nucleic acid molecules.

23 Claims, 2 Drawing Sheets

Figure 1:
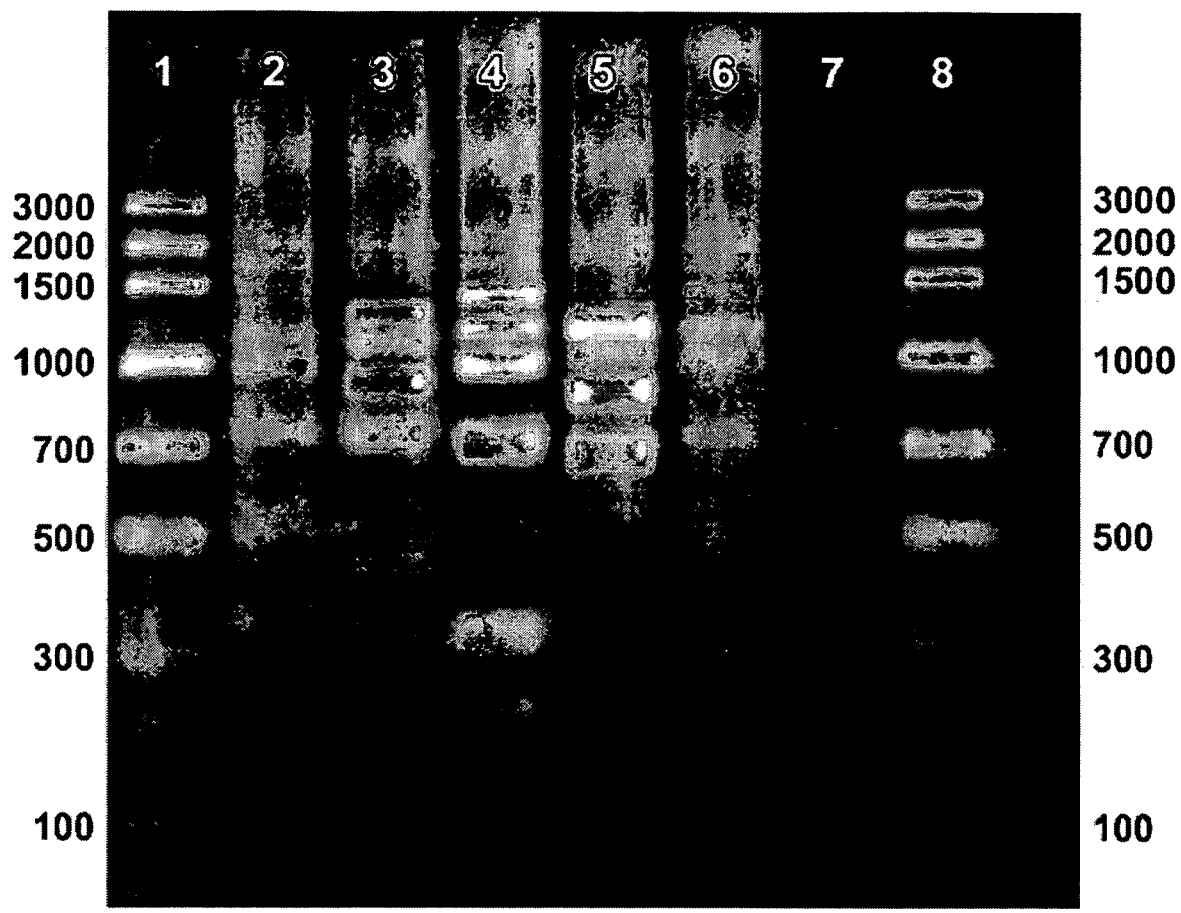

SEQUENCE LISTING

<160> NUMBER OF SEQ ID NOS: 91

<210> SEQ ID NO 1
<211> LENGTH: 106
<212> TYPE: DNA
<213> ORGANISM: Bacillus anthracis

<400> SEQUENCE: 1
tggcggaaaa gctaatatag taaagtaata attttattta tgaatttact tctaaaaagc        60
agatagaaat aaaattctag ttttagacag gagattcgat atgtgg                      106

<210> SEQ ID NO 2
<211> LENGTH: 23
<212> TYPE: DNA
<213> ORGANISM: Bacillus anthracis -continued

```
<400> SEQUENCE: 2
tggcggaaaa gctaatatag taa                                             23

<210> SEQ ID NO 3
<211> LENGTH: 26
<212> TYPE: DNA
<213> ORGANISM: Bacillus anthracis

<400> SEQUENCE: 3
ttttagacag gagattcgat atgtgg                                          26

<210> SEQ ID NO 4
<211> LENGTH: 23
<212> TYPE: DNA
<213> ORGANISM: Bacillus anthracis

<400> SEQUENCE: 4
acttctaaaa agcagataga aat                                             23

<210> SEQ ID NO 5
<211> LENGTH: 22
<212> TYPE: DNA
<213> ORGANISM: Bacillus anthracis

<400> SEQUENCE: 5
tggcggaaaa gctaatatag ta                                              22

<210> SEQ ID NO 6
<211> LENGTH: 22
<212> TYPE: DNA
<213> ORGANISM: Bacillus anthracis

<400> SEQUENCE: 6
ggcggaaaag ctaatatagt aa                                              22

<210> SEQ ID NO 7
<211> LENGTH: 22
<212> TYPE: DNA
<213> ORGANISM: Bacillus anthracis

<400> SEQUENCE: 7
gcggaaaagc taatatagta aa                                              22

<210> SEQ ID NO 8
<211> LENGTH: 22
<212> TYPE: DNA
<213> ORGANISM: Bacillus anthracis

<400> SEQUENCE: 8
cggaaaagct aatatagtaa ag                                              22

<210> SEQ ID NO 9
<211> LENGTH: 22
<212> TYPE: DNA
<213> ORGANISM: Bacillus anthracis

<400> SEQUENCE: 9
ggaaaagcta atatagtaaa gt                                              22

<210> SEQ ID NO 10
<211> LENGTH: 22
<212> TYPE: DNA
<213> ORGANISM: Bacillus anthracis
```

```
<400> SEQUENCE: 10
gaaaagctaa tatagtaaag ta                                              22

<210> SEQ ID NO 11
<211> LENGTH: 22
<212> TYPE: DNA
<213> ORGANISM: Bacillus anthracis

<400> SEQUENCE: 11
aaaagctaat atagtaaagt aa                                              22

<210> SEQ ID NO 12
<211> LENGTH: 22
<212> TYPE: DNA
<213> ORGANISM: Bacillus anthracis

<400> SEQUENCE: 12
aaagctaata tagtaaagta at                                              22

<210> SEQ ID NO 13
<211> LENGTH: 22
<212> TYPE: DNA
<213> ORGANISM: Bacillus anthracis

<400> SEQUENCE: 13
aagctaatat agtaaagtaa ta                                              22

<210> SEQ ID NO 14
<211> LENGTH: 22
<212> TYPE: DNA
<213> ORGANISM: Bacillus anthracis

<400> SEQUENCE: 14
agctaatata gtaaagtaat aa                                              22

<210> SEQ ID NO 15
<211> LENGTH: 22
<212> TYPE: DNA
<213> ORGANISM: Bacillus anthracis

<400> SEQUENCE: 15
gctaatatag taaagtaata at                                              22

<210> SEQ ID NO 16
<211> LENGTH: 22
<212> TYPE: DNA
<213> ORGANISM: Bacillus anthracis

<400> SEQUENCE: 16
ctaatatagt aaagtaataa tt                                              22

<210> SEQ ID NO 17
<211> LENGTH: 22
<212> TYPE: DNA
<213> ORGANISM: Bacillus anthracis

<400> SEQUENCE: 17
taatatagta aagtaataat tt                                              22

<210> SEQ ID NO 18
<211> LENGTH: 22
<212> TYPE: DNA
```

```
<213> ORGANISM: Bacillus anthracis

<400> SEQUENCE: 18
aatatagtaa agtaataatt tt                                              22

<210> SEQ ID NO 19
<211> LENGTH: 22
<212> TYPE: DNA
<213> ORGANISM: Bacillus anthracis

<400> SEQUENCE: 19
atatagtaaa gtaataattt ta                                              22

<210> SEQ ID NO 20
<211> LENGTH: 22
<212> TYPE: DNA
<213> ORGANISM: Bacillus anthracis

<400> SEQUENCE: 20
tatagtaaag taataatttt at                                              22

<210> SEQ ID NO 21
<211> LENGTH: 22
<212> TYPE: DNA
<213> ORGANISM: Bacillus anthracis

<400> SEQUENCE: 21
atagtaaagt aataatttta tt                                              22

<210> SEQ ID NO 22
<211> LENGTH: 22
<212> TYPE: DNA
<213> ORGANISM: Bacillus anthracis

<400> SEQUENCE: 22
tagtaaagta ataattttat tt                                              22

<210> SEQ ID NO 23
<211> LENGTH: 22
<212> TYPE: DNA
<213> ORGANISM: Bacillus anthracis

<400> SEQUENCE: 23
agtaaagtaa taattttatt ta                                              22

<210> SEQ ID NO 24
<211> LENGTH: 22
<212> TYPE: DNA
<213> ORGANISM: Bacillus anthracis

<400> SEQUENCE: 24
gtaaagtaat aattttattt at                                              22

<210> SEQ ID NO 25
<211> LENGTH: 22
<212> TYPE: DNA
<213> ORGANISM: Bacillus anthracis

<400> SEQUENCE: 25
taaagtaata attttattta tg                                              22

<210> SEQ ID NO 26
<211> LENGTH: 22
```

```
<212> TYPE: DNA
<213> ORGANISM: Bacillus anthracis

<400> SEQUENCE: 26
aaagtaataa ttttatttat ga                                          22

<210> SEQ ID NO 27
<211> LENGTH: 22
<212> TYPE: DNA
<213> ORGANISM: Bacillus anthracis

<400> SEQUENCE: 27
aagtaataat tttatttatg aa                                          22

<210> SEQ ID NO 28
<211> LENGTH: 22
<212> TYPE: DNA
<213> ORGANISM: Bacillus anthracis

<400> SEQUENCE: 28
agtaataatt ttatttatga at                                          22

<210> SEQ ID NO 29
<211> LENGTH: 22
<212> TYPE: DNA
<213> ORGANISM: Bacillus anthracis

<400> SEQUENCE: 29
gtaataattt tatttatgaa tt                                          22

<210> SEQ ID NO 30
<211> LENGTH: 22
<212> TYPE: DNA
<213> ORGANISM: Bacillus anthracis

<400> SEQUENCE: 30
taataatttt atttatgaat tt                                          22

<210> SEQ ID NO 31
<211> LENGTH: 22
<212> TYPE: DNA
<213> ORGANISM: Bacillus anthracis

<400> SEQUENCE: 31
aataatttta tttatgaatt ta                                          22

<210> SEQ ID NO 32
<211> LENGTH: 22
<212> TYPE: DNA
<213> ORGANISM: Bacillus anthracis

<400> SEQUENCE: 32
ataattttat ttatgaattt ac                                          22

<210> SEQ ID NO 33
<211> LENGTH: 22
<212> TYPE: DNA
<213> ORGANISM: Bacillus anthracis

<400> SEQUENCE: 33
taattttatt tatgaattta ct                                          22

<210> SEQ ID NO 34
```

-continued

```
<211> LENGTH: 22
<212> TYPE: DNA
<213> ORGANISM: Bacillus anthracis

<400> SEQUENCE: 34
aattttattt atgaatttac tt                                              22

<210> SEQ ID NO 35
<211> LENGTH: 22
<212> TYPE: DNA
<213> ORGANISM: Bacillus anthracis

<400> SEQUENCE: 35
attttattta tgaatttact tc                                              22

<210> SEQ ID NO 36
<211> LENGTH: 22
<212> TYPE: DNA
<213> ORGANISM: Bacillus anthracis

<400> SEQUENCE: 36
ttttatttat gaatttactt ct                                              22

<210> SEQ ID NO 37
<211> LENGTH: 22
<212> TYPE: DNA
<213> ORGANISM: Bacillus anthracis

<400> SEQUENCE: 37
tttatttatg aatttacttc ta                                              22

<210> SEQ ID NO 38
<211> LENGTH: 22
<212> TYPE: DNA
<213> ORGANISM: Bacillus anthracis

<400> SEQUENCE: 38
ttatttatga atttacttct aa                                              22

<210> SEQ ID NO 39
<211> LENGTH: 22
<212> TYPE: DNA
<213> ORGANISM: Bacillus anthracis

<400> SEQUENCE: 39
tatttatgaa tttacttcta aa                                              22

<210> SEQ ID NO 40
<211> LENGTH: 22
<212> TYPE: DNA
<213> ORGANISM: Bacillus anthracis

<400> SEQUENCE: 40
atttatgaat ttacttctaa aa                                              22

<210> SEQ ID NO 41
<211> LENGTH: 22
<212> TYPE: DNA
<213> ORGANISM: Bacillus anthracis

<400> SEQUENCE: 41
tttatgaatt tacttctaaa aa                                              22
```

```
<210> SEQ ID NO 42
<211> LENGTH: 22
<212> TYPE: DNA
<213> ORGANISM: Bacillus anthracis

<400> SEQUENCE: 42
ttatgaattt acttctaaaa ag                                              22

<210> SEQ ID NO 43
<211> LENGTH: 22
<212> TYPE: DNA
<213> ORGANISM: Bacillus anthracis

<400> SEQUENCE: 43
tatgaattta cttctaaaaa gc                                              22

<210> SEQ ID NO 44
<211> LENGTH: 22
<212> TYPE: DNA
<213> ORGANISM: Bacillus anthracis

<400> SEQUENCE: 44
atgaatttac ttctaaaaag ca                                              22

<210> SEQ ID NO 45
<211> LENGTH: 22
<212> TYPE: DNA
<213> ORGANISM: Bacillus anthracis

<400> SEQUENCE: 45
tgaatttact tctaaaaagc ag                                              22

<210> SEQ ID NO 46
<211> LENGTH: 22
<212> TYPE: DNA
<213> ORGANISM: Bacillus anthracis

<400> SEQUENCE: 46
gaatttactt ctaaaaagca ga                                              22

<210> SEQ ID NO 47
<211> LENGTH: 22
<212> TYPE: DNA
<213> ORGANISM: Bacillus anthracis

<400> SEQUENCE: 47
aatttacttc taaaaagcag at                                              22

<210> SEQ ID NO 48
<211> LENGTH: 22
<212> TYPE: DNA
<213> ORGANISM: Bacillus anthracis

<400> SEQUENCE: 48
atttacttct aaaaagcaga ta                                              22

<210> SEQ ID NO 49
<211> LENGTH: 22
<212> TYPE: DNA
<213> ORGANISM: Bacillus anthracis

<400> SEQUENCE: 49
tttacttcta aaaagcagat ag                                              22
```

```
<210> SEQ ID NO 50
<211> LENGTH: 22
<212> TYPE: DNA
<213> ORGANISM: Bacillus anthracis

<400> SEQUENCE: 50
ttacttctaa aaagcagata ga                                              22

<210> SEQ ID NO 51
<211> LENGTH: 22
<212> TYPE: DNA
<213> ORGANISM: Bacillus anthracis

<400> SEQUENCE: 51
tacttctaaa aagcagatag aa                                              22

<210> SEQ ID NO 52
<211> LENGTH: 22
<212> TYPE: DNA
<213> ORGANISM: Bacillus anthracis

<400> SEQUENCE: 52
acttctaaaa agcagataga aa                                              22

<210> SEQ ID NO 53
<211> LENGTH: 22
<212> TYPE: DNA
<213> ORGANISM: Bacillus anthracis

<400> SEQUENCE: 53
cttctaaaaa gcagatagaa at                                              22

<210> SEQ ID NO 54
<211> LENGTH: 22
<212> TYPE: DNA
<213> ORGANISM: Bacillus anthracis

<400> SEQUENCE: 54
ttctaaaaag cagatagaaa ta                                              22

<210> SEQ ID NO 55
<211> LENGTH: 22
<212> TYPE: DNA
<213> ORGANISM: Bacillus anthracis

<400> SEQUENCE: 55
tctaaaaagc agatagaaat aa                                              22

<210> SEQ ID NO 56
<211> LENGTH: 22
<212> TYPE: DNA
<213> ORGANISM: Bacillus anthracis

<400> SEQUENCE: 56
ctaaaaagca gatagaaata aa                                              22

<210> SEQ ID NO 57
<211> LENGTH: 22
<212> TYPE: DNA
<213> ORGANISM: Bacillus anthracis

<400> SEQUENCE: 57
taaaaagcag atagaaataa aa                                              22
```

```
<210> SEQ ID NO 58
<211> LENGTH: 22
<212> TYPE: DNA
<213> ORGANISM: Bacillus anthracis

<400> SEQUENCE: 58
aaaaagcaga tagaaataaa at                                           22

<210> SEQ ID NO 59
<211> LENGTH: 22
<212> TYPE: DNA
<213> ORGANISM: Bacillus anthracis

<400> SEQUENCE: 59
aaaagcagat agaaataaaa tt                                           22

<210> SEQ ID NO 60
<211> LENGTH: 22
<212> TYPE: DNA
<213> ORGANISM: Bacillus anthracis

<400> SEQUENCE: 60
aaagcagata gaaataaaat tc                                           22

<210> SEQ ID NO 61
<211> LENGTH: 22
<212> TYPE: DNA
<213> ORGANISM: Bacillus anthracis

<400> SEQUENCE: 61
aagcagatag aaataaaatt ct                                           22

<210> SEQ ID NO 62
<211> LENGTH: 22
<212> TYPE: DNA
<213> ORGANISM: Bacillus anthracis

<400> SEQUENCE: 62
agcagataga aataaaattc ta                                           22

<210> SEQ ID NO 63
<211> LENGTH: 22
<212> TYPE: DNA
<213> ORGANISM: Bacillus anthracis

<400> SEQUENCE: 63
gcagatagaa ataaaattct ag                                           22

<210> SEQ ID NO 64
<211> LENGTH: 22
<212> TYPE: DNA
<213> ORGANISM: Bacillus anthracis

<400> SEQUENCE: 64
cagatagaaa taaaattcta gt                                           22

<210> SEQ ID NO 65
<211> LENGTH: 22
<212> TYPE: DNA
<213> ORGANISM: Bacillus anthracis

<400> SEQUENCE: 65
```
agatagaaat aaaattctag tt                                           22

<210> SEQ ID NO 66
<211> LENGTH: 22
<212> TYPE: DNA
<213> ORGANISM: Bacillus anthracis

<400> SEQUENCE: 66
gatagaaata aaattctagt tt                                           22

<210> SEQ ID NO 67
<211> LENGTH: 22
<212> TYPE: DNA
<213> ORGANISM: Bacillus anthracis

<400> SEQUENCE: 67
atagaaataa aattctagtt tt                                           22

<210> SEQ ID NO 68
<211> LENGTH: 22
<212> TYPE: DNA
<213> ORGANISM: Bacillus anthracis

<400> SEQUENCE: 68
tagaaataaa attctagttt ta                                           22

<210> SEQ ID NO 69
<211> LENGTH: 22
<212> TYPE: DNA
<213> ORGANISM: Bacillus anthracis

<400> SEQUENCE: 69
agaaataaaa ttctagtttt ag                                           22

<210> SEQ ID NO 70
<211> LENGTH: 22
<212> TYPE: DNA
<213> ORGANISM: Bacillus anthracis

<400> SEQUENCE: 70
gaaataaaat tctagtttta ga                                           22

<210> SEQ ID NO 71
<211> LENGTH: 22
<212> TYPE: DNA
<213> ORGANISM: Bacillus anthracis

<400> SEQUENCE: 71
aaataaaatt ctagttttag ac                                           22

<210> SEQ ID NO 72
<211> LENGTH: 22
<212> TYPE: DNA
<213> ORGANISM: Bacillus anthracis

<400> SEQUENCE: 72
aataaaattc tagttttaga ca                                           22

<210> SEQ ID NO 73
<211> LENGTH: 22
<212> TYPE: DNA
<213> ORGANISM: Bacillus anthracis

<400> SEQUENCE: 73
ataaaattct agttttagac ag                                            22

<210> SEQ ID NO 74
<211> LENGTH: 22
<212> TYPE: DNA
<213> ORGANISM: Bacillus anthracis

<400> SEQUENCE: 74
taaaattcta gttttagaca gg                                            22

<210> SEQ ID NO 75
<211> LENGTH: 22
<212> TYPE: DNA
<213> ORGANISM: Bacillus anthracis

<400> SEQUENCE: 75
aaaattctag ttttagacag ga                                            22

<210> SEQ ID NO 76
<211> LENGTH: 22
<212> TYPE: DNA
<213> ORGANISM: Bacillus anthracis

<400> SEQUENCE: 76
aaattctagt tttagacagg ag                                            22

<210> SEQ ID NO 77
<211> LENGTH: 22
<212> TYPE: DNA
<213> ORGANISM: Bacillus anthracis

<400> SEQUENCE: 77
aattctagtt ttagacagga ga                                            22

<210> SEQ ID NO 78
<211> LENGTH: 22
<212> TYPE: DNA
<213> ORGANISM: Bacillus anthracis

<400> SEQUENCE: 78
attctagttt tagacaggag at                                            22

<210> SEQ ID NO 79
<211> LENGTH: 22
<212> TYPE: DNA
<213> ORGANISM: Bacillus anthracis

<400> SEQUENCE: 79
ttctagtttt agacaggaga tt                                            22

<210> SEQ ID NO 80
<211> LENGTH: 22
<212> TYPE: DNA
<213> ORGANISM: Bacillus anthracis

<400> SEQUENCE: 80
tctagtttta gacaggagat tc                                            22

<210> SEQ ID NO 81
<211> LENGTH: 22
<212> TYPE: DNA
<213> ORGANISM: Bacillus anthracis

```
<400> SEQUENCE: 81
ctagttttag acaggagatt cg                                          22

<210> SEQ ID NO 82
<211> LENGTH: 22
<212> TYPE: DNA
<213> ORGANISM: Bacillus anthracis

<400> SEQUENCE: 82
tagttttaga caggagattc ga                                          22

<210> SEQ ID NO 83
<211> LENGTH: 22
<212> TYPE: DNA
<213> ORGANISM: Bacillus anthracis

<400> SEQUENCE: 83
agttttagac aggagattcg at                                          22

<210> SEQ ID NO 84
<211> LENGTH: 22
<212> TYPE: DNA
<213> ORGANISM: Bacillus anthracis

<400> SEQUENCE: 84
gttttagaca ggagattcga ta                                          22

<210> SEQ ID NO 85
<211> LENGTH: 22
<212> TYPE: DNA
<213> ORGANISM: Bacillus anthracis

<400> SEQUENCE: 85
ttttagacag gagattcgat at                                          22

<210> SEQ ID NO 86
<211> LENGTH: 22
<212> TYPE: DNA
<213> ORGANISM: Bacillus anthracis

<400> SEQUENCE: 86
tttagacagg agattcgata tg                                          22

<210> SEQ ID NO 87
<211> LENGTH: 22
<212> TYPE: DNA
<213> ORGANISM: Bacillus anthracis

<400> SEQUENCE: 87
ttagacagga gattcgatat gt                                          22

<210> SEQ ID NO 88
<211> LENGTH: 22
<212> TYPE: DNA
<213> ORGANISM: Bacillus anthracis

<400> SEQUENCE: 88
tagacaggag attcgatatg tg                                          22

<210> SEQ ID NO 89
<211> LENGTH: 22
<212> TYPE: DNA
<213> ORGANISM: Bacillus anthracis
```

```
<400> SEQUENCE: 89
agacaggaga ttcgatatgt gg                                           22

<210> SEQ ID NO 90
<211> LENGTH: 20
<212> TYPE: DNA
<213> ORGANISM: Bacillus anthracis

<400> SEQUENCE: 90
agattttccg acggcaggtt                                              20

<210> SEQ ID NO 91
<211> LENGTH: 22
<212> TYPE: DNA
<213> ORGANISM: Bacillus anthracis

<400> SEQUENCE: 91
tttcaatcaa tcgcgcctta tt                                           22
```

UNIQUE CHROMOSOMAL SEQUENCE OF *BACILLUS ANTHRACIS* AND METHODS OF MAKING AND USING THEREOF INCLUDING REAL-TIME PCR ASSAYS

CROSS REFERENCE TO RELATED APPLICATIONS

This application claims the benefit of U.S. Provisional Patent Application Nos. 60/556,045 filed 24 Mar. 2004, and 60/564,639, filed 23 Apr. 2004, which names Elizabeth A. Bode, William J. Hurtle, and David A. Norwood, Jr. as inventors, both of which are herein incorporated by reference in their entirety.

ACKNOWLEDGMENT OF GOVERNMENT SUPPORT

Employees of the United States Army made this invention. The government has rights in the invention.

BACKGROUND OF THE INVENTION

1. Field of the Invention

The present invention generally relates to nucleic acid molecules of *Bacillus anthracis*. The nucleic acid molecules may be used in nucleic acid assays.

2. Description of the Related Art

*Bacillus anthracis* is a spore-forming gram-positive bacterium well known for its recent use as a bioterrorist agent. Identification of *B. anthracis* can be done clinically utilizing gram stain, colony morphology, and various biochemical tests. See Logan & Turnbull (2003) In Manual of Clinical Microbiology. American Society of Microbiology, Washington D.C. However, these methods are time consuming and more rapid tests, such as polymerase chain reaction (PCR), have been employed to detect *B. anthracis* in clinical samples. See Oggioni, et al. (2002) J. Clin. Microbiol. 40:3956-3963.

Real-time PCR is preferred over conventional PCR methods for the identification of organisms because it is fast, less labor intensive, and adds the specificity of a probe. Real-time PCR assays have been used to identify *anthracis* based on virulence genes associated with the toxin-encoding plasmid (pX01) and capsule-encoding plasmid (pX02). See Higgins, et al. (2003) Appl. Environ. Microbiol. 69:593-599; Oggioni, et al. (2002) J. Clin. Microbiol. 40:3956-3963; and Patra, et al. (2002) Ann. N.Y. Acad. Sci. 969:106-111. While the presence of both pX01 and pX02 is needed to give *B. anthracis* its virulence, it is conceivable that these plasmids could be passed to its genetic neighbors with unknown implications. Thus, a chromosomal marker for use in nucleic acid based assays such as real-time PCR assays is more desirable.

Unfortunately, past attempts at developing a chromosomal real-time PCR assay have failed due to the close genetic relationship of *Bacillus* species. *B. anthracis*, *Bacillus cereus*, and *Bacillus thuringiensis* have very little variability and are genetically indistinguishable using multilocus enzyme electrophoresis. See Helgason, et al. (2000) Appl. Environ. Microbiol. 66:2627-2630. Recent work using rep-PCR has shown that the previously listed species of *Bacillus* as well as *Bacillus mycoides*, *Bacillus pseudomycoides*, and *Bacillus weihenstephanensis* do have some genetic differences. See Cherif, et al. (2003) J. Appl. Microbiol. 94:1108-1119. A real-time PCR assay based on the chromosomal rpoB gene has been developed and used, however, it targets a region that is variable between *Bacillus* species, therefore, the specificity of the assay is dependent on PCR conditions and specific primers and probes. See Drago, et al. (2002) J. Clin. Microbiol. 40:4399; and Qi, et al. (2001) Appl. Environ. Microbiol. 67:3720-3727.

Thus, a need still exists for a unique chromosomal nucleotide sequence in *B. anthracis* for use in nucleic acid based assays such as real-time PCR assays.

SUMMARY OF THE INVENTION

The present invention generally relates to nucleic acid molecules that are specific for *Bacillus anthracis*.

In some embodiments, the present invention provides an isolated nucleic acid molecule comprising at least about 11 consecutive nucleotides of the sequence set forth in SEQ ID NO:1 or its complement. In some embodiments, the nucleic acid molecule comprises (a) at least about 22 consecutive nucleotides of the sequence set forth in SEQ ID NO:1 or its complement;
(b) at least about 30 consecutive nucleotides of the sequence set forth in SEQ ID NO:1 or its complement;
(c) at least about 40 consecutive nucleotides of the sequence set forth in SEQ ID NO:1 or its complement;
(d) at least about 50 consecutive nucleotides of the sequence set forth in SEQ ID NO:1 or its complement;
(e) at least about 60 consecutive nucleotides of the sequence set forth in SEQ ID NO:1 or its complement;
(f) at least about 70 consecutive nucleotides of the sequence set forth in SEQ ID NO:1 or its complement;
(g) at least about 80 consecutive nucleotides of the sequence set forth in SEQ ID NO:1 or its complement;
(h) at least about 90 consecutive nucleotides of the sequence set forth in SEQ ID NO:1 or its complement;
(i) at least about 100 consecutive nucleotides of the sequence set forth in SEQ ID NO:1 or its complement; or
(j) the sequence set forth in SEQ ID NO:1 or its complement.

In some embodiments, the present invention provides a nucleic acid molecule of which consists essentially of at least about 11 consecutive nucleotides of the sequence set forth in SEQ ID NO:1 or its complement. In some embodiments, the nucleic acid molecule consists essentially of (a) at least about 22 consecutive nucleotides of the sequence set forth in SEQ ID NO:1 or its complement;
(b) at least about 30 consecutive nucleotides of the sequence set forth in SEQ ID NO:1 or its complement;
(c) at least about 40 consecutive nucleotides of the sequence set forth in SEQ ID NO:1 or its complement;
(d) at least about 50 consecutive nucleotides of the sequence set forth in SEQ ID NO:1 or its complement;
(e) at least about 60 consecutive nucleotides of the sequence set forth in SEQ ID NO:1 or its complement;
(f) at least about 70 consecutive nucleotides of the sequence set forth in SEQ ID NO:1 or its complement;
(g) at least about 80 consecutive nucleotides of the sequence set forth in SEQ ID NO:1 or its complement;
(h) at least about 90 consecutive nucleotides of the sequence set forth in SEQ ID NO:1 or its complement;
(i) at least about 100 consecutive nucleotides of the sequence set forth in SEQ ID NO:1 or its complement; or
(j) the sequence set forth in SEQ ID NO:1 or its complement.

In some embodiments, the present invention provides a nucleic acid molecule which consists of at least about 11 consecutive nucleotides of the sequence set forth in SEQ ID NO:1 or its complement. In some embodiments, the nucleic acid molecule consists of (a) at least about 22 consecutive nucleotides of the sequence set forth in SEQ ID NO:1 or its complement;
(b) at least about 30 consecutive nucleotides of the sequence set forth in SEQ ID NO:1 or its complement;
(c) at least about 40 consecutive nucleotides of the sequence set forth in SEQ ID NO:1 or its complement;
(d) at least about 50 consecutive nucleotides of the sequence set forth in SEQ ID NO:1 or its complement;
(e) at least about 60 consecutive nucleotides of the sequence set forth in SEQ ID NO:1 or its complement;
(f) at least about 70 consecutive nucleotides of the sequence set forth in SEQ ID NO:1 or its complement;
(g) at least about 80 consecutive nucleotides of the sequence set forth in SEQ ID NO:1 or its complement;
(h) at least about 90 consecutive nucleotides of the sequence set forth in SEQ ID NO:1 or its complement;
(i) at least about 100 consecutive nucleotides of the sequence set forth in SEQ ID NO:1 or its complement; or
(j) the sequence set forth in SEQ ID NO:1 or its complement.

In some embodiments, the present invention provides an isolated nucleic acid molecule that has a sequence identity of at least about 90% over
(a) at least about 11 consecutive nucleotides of the sequence set forth in SEQ ID NO:1 or its complement;
(b) at least about 22 consecutive nucleotides of the sequence set forth in SEQ ID NO:1 or its complement;
(c) at least about 30 consecutive nucleotides of the sequence set forth in SEQ ID NO:1 or its complement;
(d) at least about 40 consecutive nucleotides of the sequence set forth in SEQ ID NO:1 or its complement;
(e) at least about 50 consecutive nucleotides of the sequence set forth in SEQ ID NO:1 or its complement;
(f) at least about 60 consecutive nucleotides of the sequence set forth in SEQ ID NO:1 or its complement;
(g) at least about 70 consecutive nucleotides of the sequence set forth in SEQ ID NO:1 or its complement;
(h) at least about 80 consecutive nucleotides of the sequence set forth in SEQ ID NO:1 or its complement;
(i) at least about 90 consecutive nucleotides of the sequence set forth in SEQ ID NO:1 or its complement;
(j) at least about 100 consecutive nucleotides of the sequence set forth in SEQ ID NO:1 or its complement; or
(k) the sequence set forth in SEQ ID NO:1 or its complement.

In some embodiments, the present invention provides an isolated nucleic acid molecule that has a sequence identity of at least about 98% over (a) at least about 11 consecutive nucleotides of the sequence set forth in SEQ ID NO:1 or its complement;
(b) at least about 15 consecutive nucleotides of the sequence set forth in SEQ ID NO:1 or its complement;
(c) at least about 20 consecutive nucleotides of the sequence set forth in SEQ ID NO:1 or its complement;
(d) at least about 30 consecutive nucleotides of the sequence set forth in SEQ ID NO:1 or its complement;
(e) at least about 40 consecutive nucleotides of the sequence set forth in SEQ ID NO:1 or its complement;
(f) at least about 50 consecutive nucleotides of the sequence set forth in SEQ ID NO:1 or its complement;
(g) at least about 60 consecutive nucleotides of the sequence set forth in SEQ ID NO:1 or its complement;
(h) at least about 70 consecutive nucleotides of the sequence set forth in SEQ ID NO:1 or its complement;
(i) at least about 80 consecutive nucleotides of the sequence set forth in SEQ ID NO:1 or its complement;
(j) at least about 90 consecutive nucleotides of the sequence set forth in SEQ ID NO:1 or its complement;
(k) at least about 100 consecutive nucleotides of the sequence set forth in SEQ ID NO:1 or its complement; or
(l) the sequence set forth in SEQ ID NO:1 or its complement.

In some embodiments, the present invention provides a probe comprising an isolated nucleic acid molecule provided herein and a label.

In some embodiments, the present invention provides a probe comprising an isolated nucleic acid molecule provided herein, a reporter molecule, and a quencher molecule. In some embodiments, the reporter molecule produces a signal upon the separation of the reporter molecule and the quencher molecule. In some embodiments, the quencher molecule is capable of quenching the signal of the reporter molecule. In some embodiments, the reporter molecule is a fluorophore, such as FAM, ROX, TEXAS RED, TET, TAMRA, JOE, HEX, CAL RED, or VIC. In some embodiments, the probe is capable of being cleaved by a protein thereby separating the reporter molecule from the quencher molecule. In some embodiments, the protein is Taq polymerase.

In some embodiments, the present invention provides an assay which comprises using a probe according to the present invention. In some embodiments, the assay is a nucleic acid hybridization assay. In some embodiments, the assay is a TaqMan® based assay. In some embodiments, the assay further comprises conducting PCR amplification. In some embodiments, the assay further comprises detecting the presence or measuring the amount of the probe and detecting the presence or measuring the amount of a target nucleic acid molecule. In some embodiments, the absence of the target nucleic acid molecule and the absence of the probe indicate a true negative result for the target nucleic acid molecule. In some embodiments, the absence of the target nucleic acid molecule and the presence of the probe indicate a false negative result for the target nucleic acid molecule. In some embodiments, the assay provides about 100% specificity to *Bacillus anthracis*. In some embodiments, the assay provides about 100% sensitivity to *Bacillus anthracis*.

In some embodiments, the present invention provides a kit for a probe-based nucleic acid assay comprising an isolated nucleic acid molecule provided herein packaged with instructions for use. In some embodiments, the isolated nucleic acid molecule contains a label. In some embodiments, the label is a reporter molecule and a quencher molecule. In some embodiments, the probe-based nucleic acid assay is for the detection of an organism. In some embodiments, the organism belongs to *Bacillus*. In some embodiments, the organism is *Bacillus anthracis*. In some embodiments, the kit further comprises reagents or components for detecting the presence of a nucleic acid molecule belonging to the organism.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 shows a gel of DNA products following nested PCR. Lanes 1 and 8, DNA PCR ladder (Gene Choice, Frederick, Md.); lane 2, subtracted Delta ANR-SWS *B. anthracis*; lane 3, unsubtracted Delta ANR-SWS *B. anthracis*; lane 4, subtracted *Escherichia coli*; lane 5, unsubtracted *Escherichia coli*; lane 6, subtracted control *Escherichia coli*; lane 7, empty.

Figure 2:
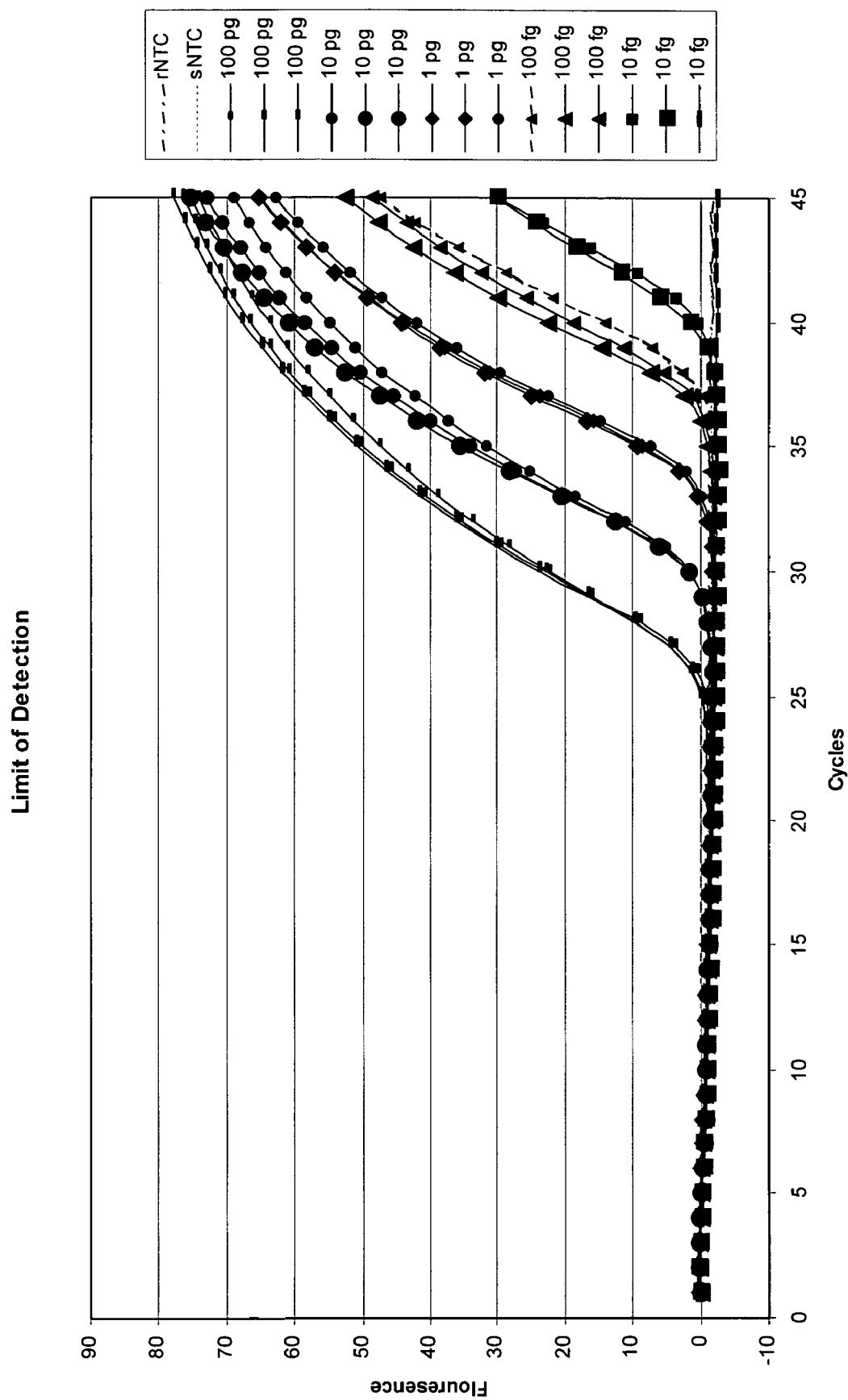

FIG. 2 shows real-time PCR results to determine efficacy.

DETAILED DESCRIPTION OF THE INVENTION

The present invention provides a novel chromosomal *Bacillus anthracis* nucleic acid sequence (SEQ ID NO:1)
5'<u>TGGCGGAAAAGCTAATATAGTAAA</u>GTAATAATTTTATTTATGAATTT ACTTCTAAAAAGCAGATAGAAATAAAATTCTAG<u>TTTTAGACAGGAGATTC GATATGTGG</u>3' which may be used in nucleic acid based assays, such as real-time PCR assays, for detecting *B. anthracis* in a sample. Also provided are primers and probes for detecting the novel chromosomal *B. anthracis* nucleic acid sequence. As shown above, the underlined portions of the sequence indicate primer F41 and primer R146 and are respectively designated as SEQ ID NO:2 and SEQ ID NO:3, and the bold face portion of the sequence indicates probe P88 and is designated as SEQ ID NO:4.

As described herein, nucleic acid isolated from *B. cereus* (strain ATCC 21769, Manassas, Va.) and genomic DNA from plasmid-cured *B. anthracis* strain Delta ANR-SWS was used in a genomic subtraction hybridization to identify possible chromosomal sequences unique to *B. anthracis* that could be used to develop a real-time PCR assay according to methods known in the art and described in the Examples below. See Emmerth, et al. (1999) J. Bacteriol. 181:5652-5661; Pradel, et al. (2002) Appl. Environ. Microbiol. 68:2316-2325; and Radnedge, et al. (2003) Appl. Environ. Microbiol. 69:2755-2764, which are herein incorporated by reference.

Differentiation of *B. anthracis* from its close relatives has traditionally relied upon phenotypic characterization determined in a clinical setting. See Hoffmaster, et al. (2002) Emerg. Infect. Dis. 8:1178-1182, which is herein incorporated by reference. However, these methods can often take from 24 to 48 hours to complete. See Logan & Turnbull (2003) In Manual of Clinical Microbiology. American Society of Microbiology, Washington D.C., which is herein incorporated by reference. Recently, increased awareness about biological weapons and the use of anthrax as a bioterrorist agent have led to the necessity for improved and more rapid methods of identification. See Hoffmaster, et al. (2002) Emerg. Infect. Dis. 8:1178-1182; Inglesby, et al. (1999) JAMA 281:1735-1745; and Richards, et al. (1999) Ann. Emerg. Med. 34:183-190, which are herein incorporated by reference. Real-time PCR assays may offer improved identification of *B. anthracis* due to their speed, specificity, sensitivity, and throughput. After the 2001 anthrax mailings, many of these developed, rapid PCR assays for *B. anthracis* were employed to confirm the presence or absence of the organism. See Higgins, et al. (2003) Appl. Environ. Microbiol. 69:593-599, which is herein incorporated by reference.

The the need for a *B. anthracis* chromosomal assay is due to the discovery of pX01 and pX02 cured isolates. See Ramisse, et al. (1996) FEMS Microbiol. Lett. 145:9-16; and Turnbull, et al. (1992) J. Appl. Bacteriol. 72:21-28, which are herein incorporated by reference. Identification of a virulent *B. anthracis* could be a potential indicator of virulent strains in the environment. See Turnbull, et al. (1992) J. Appl. Bacteriol. 72:21-28, which is herein incorporated by reference. To date, the majority of *B. anthracis* targets for real-time PCR assays have been developed from genes located on the pX01 and pX02 plasmids. See Bell, et al. (2002) J. Clin. Microbiol. 40:2897-2902; Ellerbrok, et al. (2002) FEMS Microbiol. Lett. 214:51-59; and Oggioni, et al. (2002) J. Clin. Microbiol. 40:3956-3963, which are herein incorporated by reference. These assays are specific because the targets code for toxins and capsule proteins essential for virulence. However, complete identification of anthrax should involve detection of both plasmids and a chromosomal marker due to the possibility of transmission, transfer, or loss of one or both plasmids between *Bacillus* species seen both in vivo and in vitro. See Koehler (2002) Curr. Top. Microbiol. Immunol. 271:143-164; Ramisse, et al. (1996) FEMS Microbiol. Lett. 145:9-16; Reddy, et al. (1987) J. Bacteriol. 169:5263-5270; and Turnbull, et al. (1992) J. Appl. Bacteriol. 72:21-28, which are herein incorporated by reference. Bioengineering may also allow the transfer of virulence plasmids to other species including bioengineered organisms, exemplifying the need to detect these man-made agents. See Hoffmaster, et al. (2002) Emerg. Infect. Dis. 8:1178-1182, which is herein incorporated by reference.

Real-time PCR assays based on chromosomal markers could provide a powerful tool for identifying samples containing *B. anthracis* whether or not any virulence plasmids are present. Development of chromosomal real-time PCR assays has been slow due to the genetic similarities between *B. anthracis* and its neighbors. See Helgason, et al. (2000) Appl. Environ. Microbiol. 66:2627-2630, which is herein incorporated by reference. To date, there are very few chromosomal markers that may be used to distinguish *B. anthracis* from its close relatives. Analysis of the 16S rDNA from *B. anthracis, B. cereus, B. mycoides,* and *B. thuringiensis* revealed almost identical sequences and some argue that due to the similarity of the *B. anthracis, B. thuringiensis,* and *B. cereus* genomes, they should be considered as belonging to the same species. See Harrell, et al. (1995) J. Clin. Microbiol. 33:1847-1850; and Helgason, et al. (2000) Appl. Environ. Microbiol. 66:2627-2630, which are herein incorporated by reference. Some chromosomal markers are available, such as the Ba813 fragment and the vrrA variable number tandem repeat (VNTR). Unfortunately, these markers have failed because they are not specific to *B. anthracis* and require extra steps after the PCR reaction making them impractical for rapid identification of *B. anthracis*. See Andersen, et al. (1996) J. Bacteriol. 178:377-384; Daffonchio, et al. (1999) Appl. Environ. Microbiol. 65:1298-1303; Hoffmaster, et al. (2002) Emerg. Infect. Dis. 8:1178-1182; Jackson, et al. (1997) Appl. Environ. Microbiol. 63:1400-1405; Keim, et al. (2000) J. Bacteriol. 182:2928-2936; Patra, et al. (1996) FEMS Immunol. Med. Microbiol. 15:223-231; Richards, et al. (1999) Ann. Emerg. Med. 34:183-190, which are herein incorporated by reference.

Recently, the rpoB gene located on the chromosome of *B. anthracis* has been targeted for the development of a real-time PCR assay. See Qi, et al. (2001) Appl. Environ. Microbiol. 67:3720-3727, which is herein incorporated by reference. This rpoB gene assay is based upon a theoretical difference in melting temperature due to single nucleotide differences, but in practice, the assay produces false positives. See Ellerbrok, et al. (2002) FEMS Microbiol. Lett.

214:51-59; and Qi, et al. (2001) Appl. Environ. Microbiol. 67:3720-3727, which is herein incorporated by reference.

The unique chromosomal sequence of *B. anthracis*, as provided herein as SEQ ID NO:1, was found by subtractive hybridization incorporating a plasmid-cured *B. anthracis* (tester) strain and a *Bacillus cereus* (driver) isolate using methods known in the art. See Emmerth, et al. (1999) J. Bacteriol. 181:5652-5661; Pradel, et al. (2002) Appl. Environ. Microbiol. 68:2316-2325; and Radnedge, et al. (2003) Appl. Environ. Microbiol. 69:2755-2764, which are herein incorporated by reference. Prior art forward and reverse primers, as well as, the reverse complements were checked for alignment and sequence identity with that of the present invention without success. As provided herein, use of the unique chromosomal sequence of the present invention in a chromosomal real-time PCR assay provides about 100% sensitivity to all *B. anthracis* strains studied and about 100% specificity when tested against other *Bacillus* species.

The recent release of the *B. anthracis* genome allowed for the BLAST comparison of the B26 clone sequence against this new information. Forward primer F41 and probe P88 produced significant alignments with *B. anthracis* strain AMES and strain Sterne, having the highest scores compared to any other alignment and E values of about $7\times10^{-4}$. Reverse primer R146 also produced the highest score values with *B. anthracis* strain AMES and strain Sterne with E values of about $2\times10^{-5}$, however, an alignment to *B. cereus* ATCC 10987 with an E value of about 0.005 also occurred. This *B. cereus* has been tested and is not detected by the assay. A BLAST search of the assay sequence and surrounding nucleotides (527 nucleotides total) against all protein sequences produced a high score of 191 with an E-value of about $5\times10^{-48}$ with an abhydrolase (alpha/beta hydrolase) fold for *B. anthracis* (Accession number NP_656566.1). The 106 base pair product produced in this investigation is just outside the open reading frame of this protein. Other significant alignments included a prolyl aminopeptidase of an Oceanobacillus iheyensis with a score of 115 and an E-value of about $2\times10^{-29}$ and a proline iminopeptidase of *Bacillus cereus* ATCC 14579 with a score of 94 and an E-value of about $4\times10^{-21}$.

While diversity among *B. anthracis* isolates has shown little variability using amplified fragment length polymorphism analysis, previous work using multiple-locus VNTR has classified *B. anthracis* into 89 genotypes. See Keim, et al. (1997) J. Bacteriol. 179:818-824; and Keim, et al. (2000) J. Bacteriol. 182:2928-2936. Recent sequencing on an isolate from a *B. anthracis* victim of the 2001 anthrax attack has revealed single nucleotide polymorphisms, insertions, deletions, and changes in tandem repeats when compared to reference *B. anthracis* strains. See Read, et al. (2002) Science 296:2028-2033.

However, the findings provided herein demonstrate a sensitive and specific assay for the identification of the *Bacillus anthracis* chromosome. The assay did not cross-react with any genetic neighbors available for the study and all strains of *B. anthracis* were identified. The assay was independent of plasmid profile and had a detection limit of about 50 fg. In summary, the assay developed from the sequence identified in this study is a rapid, sensitive, and specific tool for the identification of *Bacillus anthracis*.

As used herein, "nucleic acid molecule", "polynucleotide", and "oligonucleotide" are used interchangeably to refer DNA and RNA molecules of natural or synthetic origin which may be single-stranded or double-stranded, and represent the sense or antisense strand. The nucleic acid molecules of the present invention may contain known nucleotide analogs or modified backbone residues or linkages, and any substrate that can be incorporated into a polymer by DNA or RNA polymerase. Examples of such analogs inlude phospborothioates, phosphoramidates, methyl phosphonates, chiral-methyl phosphonates, 2-O-methyl ribonucleotides, peptide-nucleic acids (PNAs), and the like.

In preferred embodiments, the nucleic acid molecule of the present invention is isolated. As used herein, "isolated" refers to a nucleic acid molecule that is isolated from its native environment. An "isolated" nucleic acid molecule may be substantially isolated or purified from the genomic DNA of the species from which the nucleic acid molecule was obtained. An "isolated" polynucleotide may include a nucleic acid molecule that is separated from other DNA segments with which the nucleic acid molecule is normally or natively associated with at either the 5' end, 3' end, or both.

The nucleic acid molecules of the present invention may be in its native form or synthetically modified. The nucleic acid molecules of the present invention may be single-stranded (coding or antisense) or double-stranded, and may be DNA (genomic, cDNA or synthetic) or RNA molecules. RNA molecules include mRNA molecules, which contain introns and correspond to a DNA molecule in a one-to-one manner, and mRNA molecules, which do not contain introns. The nucleic acid molecules of the present invention may be linked to other nucleic acid molecules, support materials, reporter molecules, quencher molecules, or a combination thereof. Other nucleic acid molecules include promoters, polyadenylation signals, additional restriction enzyme sites, multiple cloning sites, other coding segments, and the like. It is therefore contemplated that a nucleic acid fragment of almost any length may be employed, with the total length preferably being limited by the ease of preparation and use in the intended recombinant DNA or PCR protocol. In some embodiments of the present invention, nucleic acid sequences comprising a nucleic acid molecule described herein are contemplated.

The nucleic acid molecules of the present invention may be readily prepared by methods known in the art, for example, directly synthesizing the nucleic acid sequence using methods and equipment known in the art such as automated oligonucleotide synthesizers, PCR technology, recombinant DNA techniques, and the like.

The nucleic acid molecules of the present invention may contain a label such as quencher molecule and a reporter molecule. A wide variety of labels and conjugation techniques are known by those skilled in the art and may be used in various nucleic acid and amino acid assays employing the nucleic acid molecules of the present invention. As used herein a "label" or a "detectable moiety" is a composition that is detectable by spectroscopic, photochemical, biochemical, immunochemical, or chemical means. A "labeled" nucleic acid molecule comprises a bound label such that the presence of the nucleic acid molecule may be detected by detecting the presence of the label bound to thereto. The label may be bound to the nucleic acid molecule via a covalent bond, such as a chemical bond, or a noncovalent bond, such as ionic, van der Waals, electrostatic, or hydrogen bonds. Methods known in the art for producing labeled hybridization or PCR probes for detecting sequences related to polynucleotides may be used and include oligolabeling, nick translation, end-labeling or PCR amplification using a labeled nucleotide, and the like, preferably end-labeling. Suitable reporter molecules and quencher molecules that may be used include radionucleotides, enzymes, fluorescent, chemiluminescent, or chromogenic agents as well as substrates, cofactors, inhibitors, magnetic particles, and the like. In preferred embodiments, a fluorescent reporter molecule and quencher molecule are used.

As used herein, a "nucleic acid probe" and "probe" refers to a nucleic acid molecule that is capable of binding to a target nucleic acid molecule having a sequence that is complementary to the sequence of the nucleic acid probe. A probe may include natural or modified bases known in the art. See e.g. MPEP 2422, 8th ed., which is herein incorporated by reference. The nucleotide bases of the probe may be joined by a linkage other than a phosphodiester bond, so long as the linkage does not interfere with the ability of the nucleic acid molecule to bind a complementary nucleic acid molecule. The probe may bind a target sequence that is less than 100% complementary to the probe sequence and such binding depends upon the stringency of the hybridization conditions. The presence or absence of the probe may be detected to determine the presence or absence of a target sequence or subsequence in a sample. The probe may contain a label whose signal is detectable by methods known in the art. As used herein a "signal" is a measurable characteristic. Where the label is a reporter molecule and a quencher molecule, the signal may increase or decrease upon dissociation of reporter molecule and the quencher molecule. For example, if the reporter molecule is a fluorophore, separation of the quencher from the fluorophore will generate a detectable signal due to an increase in light energy emitted by the fluorophore in response to illumination.

As used herein, a "target" nucleic acid molecule may be any nucleic acid molecule, the presence and/or amount of which is desired to be known. In some embodiments, the sequence of the target nucleic acid molecule is known. In some embodiments, e.g., mutation detection, the sequence of the target nucleic acid molecule may be a sequence that is suspected of having alterations, i.e. differences, from a reference nucleic acid sequence. In these embodiments, the sequence of the target nucleic acid molecule may or may not be known, and the "reference nucleic acid sequence" is a known nucleic acid sequence to which the sequence of the target nucleic acid molecule may be compared. The alteration in the target nucleic acid molecule may be in a single nucleotide base or more than a single nucleotide base. Such an alteration may be a known polymorphic alteration, such as a single nucleotide polymorphism.

The present invention provides methods to detect *B. anthracis* by amplifying or hybridizing, for example, a nucleic acid molecule comprising at least about 11 or more consecutive nucleotides, preferably at least about 22 or more consecutive nucleotides, more preferably at least about 30 or more consecutive nucleotides, even more preferably at least about 50 or more consecutive nucleotides, or most preferably all 106 nucleotides of SEQ ID NO:1. Table 1 provides a list of some preferred nucleic acid molecules of the present invention:

TABLE 1

| | |
|---|---|
| TGGCGGAAAAGCTAATATAGTA | (SEQ ID NO:5) |
| GGCGGAAAAGCTAATATAGTAA | (SEQ ID NO:6) |
| GCGGAAAAGGTAATATAGTAAA | (SEQ ID NO:7) |
| CGGAAAAGCTAATATAGTAAAG | (SEQ ID NO:8) |
| GGAAAAGCTAATATAGTAAAGT | (SEQ ID NO:9) |

TABLE 1-continued

| | |
|---|---|
| GAAAAGCTAATATAGTAAAGTA | (SEQ ID NO:10) |
| AAAAGCTAATATAGTAAAGTAA | (SEQ ID NO:11) |
| AAAGCTAATATAGTAAAGTAAT | (SEQ ID NO:12) |
| AAGCTAATATAGTAAAGTAATA | (SEQ ID NO:13) |
| AGCTAATATAGTAAAGTAATAA | (SEQ ID NO:14) |
| GCTAATATAGTAAAGTAATAAT | (SEQ ID NO:15) |
| CTAATATAGTAAAGTAATAATT | (SEQ ID NO:16) |
| TAATATAGTAAAGTAATAATTT | (SEQ ID NO:17) |
| AATATAGTAAAGTAATAATTTT | (SEQ ID NO:18) |
| ATATAGTAAAGTAATAATTTTA | (SEQ ID NO:19) |
| TATAGTAAACTAATAATTTTAT | (SEQ ID NO:20) |
| ATAGTAAAGTAATAATTTTATT | (SEQ ID NO:21) |
| TAGTAAAGTAATAATTTTATTT | (SEQ ID NO:22) |
| AGTAAAGTAATAATTTTATTTA | (SEQ ID NO:23) |
| GTAAAGTAATAATTTTATTTAT | (SEQ ID NO:24) |
| TAAAGTAATAATTTTATTTATG | (SEQ ID NO:25) |
| AAAGTAATAATTTTATTTATGA | (SEQ ID NO:26) |
| AAGTAATAATTTTATTTATGAA | (SEQ ID NO:27) |
| AGTAATAATTTTATTTATGAAT | (SEQ ID NO:28) |
| GTAATAATTTTATTTATGAATT | (SEQ ID NO:29) |
| TAATAATTTTATTTATGAATTT | (SEQ ID NO:30) |
| AATAATTTTATTTATGAATTTA | (SEQ ID NO:31) |
| ATAATTTTATTTATGAATTTAC | (SEQ ID NO:32) |
| TAATTTTATTTATGAATTTACT | (SEQ ID NO:33) |
| AATTTTATTTATGAATTTACTT | (SEQ ID NO:34) |
| ATTTTATTTATGAATTTACTTC | (SEQ ID NO:35) |
| TTTTATTTATGAATTTACTTCT | (SEQ ID NO:36) |
| TTTATTTATGAATTTACTTCTA | (SEQ ID NO:37) |
| TTATTTATGAATTTACTTCTAA | (SEQ ID NO:38) |
| TATTTATGAATTTACTTCTAAA | (SEQ ID NO:39) |
| ATTTATGAATTTACTTCTAAAA | (SEQ ID NO:40) |
| TTTATGAATTTACTTCTAAAAA | (SEQ ID NO:41) |
| TTATGAATTTACTTCTAAAAAG | (SEQ ID NO:42) |
| TATGAATTTACTTCTAAAAAGC | (SEQ ID NO:43) |
| ATGAATTTACTTCTAAAAAGCA | (SEQ ID NO:44) |
| TGAATTTACTTCTAAAAAGCAG | (SEQ ID NO:45) |
| GAATTTACTTCTAAAAAGCAGA | (SEQ ID NO:46) |
| AATTTACTTCTAAAAAGCAGAT | (SEQ ID NO:47) |
| ATTTACTTCTAAAAAGCAGATA | (SEQ ID NO:48) |
| TTTACTTCTAAAAAGCAGATAG | (SEQ ID NO:49) |

TABLE 1-continued

| | |
|---|---|
| TTACTTCTAAAAAGCAGATAGA | (SEQ ID NO:50) |
| TACTTCTAAAAAGCAGATAGAA | (SEQ ID NO:51) |
| ACTTCTAAAAAGCAGATAGAAA | (SEQ ID NO:52) |
| CTTCTAAAAAGCAGATAGAAAT | (SEQ ID NO:53) |
| TTCTAAAAAGCAGATAGAAATA | (SEQ ID NO:54) |
| TCTAAAAAGCAGATAGAAATAA | (SEQ ID NO:55) |
| CTAAAAAGCAGATAGAAATAAA | (SEQ ID NO:56) |
| TAAAAAGCACATAGAAATAAAA | (SEQ ID NO:57) |
| AAAAAGCAGATAGAAATAAAAT | (SEQ ID NO:58) |
| AAAAGCAGATAGAAATAAAATT | (SEQ ID NO:59) |
| AAAGCAGATAGAAATAAAATTC | (SEQ ID NO:60) |
| AAGCAGATAGAAATAAAATTCT | (SEQ ID NO:61) |
| AGCAGATAGAAATAAAATTCTA | (SEQ ID NO:62) |
| GCAGATAGAAATAAAATTCTAG | (SEQ ID NO:63) |
| CAGATAGAAATAAAATTCTAGT | (SEQ ID NO:64) |
| AGATAGAAATAAAATTCTAGTT | (SEQ ID NO:65) |
| GATAGAAATAAAATTCTAGTTT | (SEQ ID NO:66) |
| ATAGAAATAAAATTCTAGTTTT | (SEQ ID NO:67) |
| TAGAAATAAAATTGTAGTTTTA | (SEQ ID NO:68) |
| AGAAATAAAATTCTAGTTTTAG | (SEQ ID NO:69) |
| GAAATAAAATTCTAGTTTTAGA | (SEQ ID NO:70) |
| AAATAAAATTCTAGTTTTAGAC | (SEQ ID NO:71) |
| AATAAAATTCTAGTTTTAGACA | (SEQ ID NO:72) |
| ATAAAATTCTAGTTTTAGACAG | (SEQ ID NO:73) |
| TAAAATTCTAGTTTTAGACAGG | (SEQ ID NO:74) |
| AAAATTCTAGTTTTAGACAGGA | (SEQ ID NO:75) |
| AAATTCTAGTTTTAGACAGGAG | (SEQ ID NO:76) |
| AATTCTAGTTTTAGACAGGAGA | (SEQ ID NO:77) |
| ATTCTAGTTTTAGACAGGAGAT | (SEQ ID NO:78) |
| TTCTAGTTTTAGACAGGAGATT | (SEQ ID NO:79) |
| TCTAGTTTTAGACAGGAGATTC | (SEQ ID NO:80) |
| CTAGTTTTAGACAGGAGATTCG | (SEQ ID NO:81) |
| TAGTTTTAGACAGGAGATTCGA | (SEQ ID NO:82) |
| AGTTTTAGACAGGAGATTCGAT | (SEQ ID NO:83) |
| GTTTTAGACAGGACATTCGATA | (SEQ ID NO:84) |
| TTTTAGACAGGAGATTCGATAT | (SEQ ID NO:85) |
| TTTAGACAGGAGATTCGATATG | (SEQ ID NO:86) |
| TTAGACAGGAGATTCGATATGT | (SEQ ID NO:87) |

TABLE 1-continued

| | |
|---|---|
| TAGACAGGAGATTCGATATGTG | (SEQ ID NO:88) |
| AGACAGGAGATTCGATATGTGG | (SEQ ID NO:89) |

In some embodiments, the nucleic acid molecules of the present invention comprise at least one of the nucleic acid molecules set forth in SEQ ID NOs:1-91, or a complement thereof. In some embodiments, the nucleic acid molecules of the present invention consist essentially of at least one of the nucleic acid molecules set forth in SEQ ID NOs:1-91, or a complement thereof. In some embodiments, the nucleic acid molecules of the present invention consist of the nucleic acid molecules set forth in SEQ ID NOs:1-91, or a complement thereof. The assays of the present invention may be used to determine whether a subject has anthrax including cutaneous anthrax, gastrointestinal anthrax, oropharyngeal anthrax, inhalational anthrax, and anthrax meningitis.

The hybridization conditions may be less stringent than the conditions exemplified herein. For example, the magnesium chloride concentration, temperature, and the like may be modified according to methods known in the art in order to make the conditions less stringent. It should be noted, however, that the changes in stringency may affect assay sensitivity and specificity.

Primers and probes for use according to the present invention can be designed using, for example, a computer program such as OLIGO (Molecular Biology Insights, Inc., Cascade, Colo.). Important features when designing oligonucleotides to be used as amplification primers include an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). In preferred embodiments, the oligonucleotide primers and probes according to the present invention are about 11 to about 30 nucleotides in length, preferably about 12 to about 25 nucleotides in length, more preferably about 22 to about 25 nucleotides in length.

Designing oligonucleotides to be used as hybridization probes can be performed in a manner similar to the design of primers, although the members of a pair of probes preferably anneal to an amplification product within no more than 5 nucleotides of each other on the same strand such that FRET can occur, e.g., within no more than 1, 2, 3, or 4 nucleotides of each other. This minimal degree of separation typically brings the respective fluorescent moieties into sufficient proximity such that FRET occurs. It is to be understood, however, that other separation distances, e.g., 6 or more nucleotides, are possible provided the fluorescent moieties are appropriately positioned relative to each other, e.g., with a linker arm, such that FRET can occur. In addition, probes can be designed to hybridize to targets that contain a polymorphism or mutation, thereby allowing differential detection of B. anthracis strains based on either absolute hybridization of different pairs of probes corresponding to the particular B. anthracis strain to be distinguished or differential melting temperatures between, e.g., members of a pair of probes and each amplification product corresponding to a B. anthracis strain to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally about 15 to about 30 nucleotides in length.

Constructs of the invention include vectors containing the nucleic acid molecules disclosed herein as well as fragments thereof, e.g., at least 11 or more consecutive nucleotides of SEQ ID NO:1. Constructs of the invention can be used, for example, as control template nucleic acid molecules. Vectors suitable for use in the present invention are commercially available and/or produced by recombinant DNA technology methods routine in the art. The nucleic acid molecules disclosed herein can be obtained, for example, by chemical synthesis, direct cloning from B. anthracis, or by PCR amplification. The nucleic acid molecules of the present invention can be operably linked to a promoter or other regulatory element such as an enhancer sequence, a response element, or an inducible element that modulates expression of the nucleic acid molecule.

As used herein, "operably linking" refers to connecting a promoter and/or other regulatory elements to a given nucleic acid molecule in such a way as to permit and/or regulate expression of the nucleic acid molecule. For example, a promoter that does not normally direct expression of a nucleic acid molecule disclosed herein can be used to direct transcription of the nucleic acid molecule using, for example, a viral polymerase, a bacterial polymerase, or a eukaryotic RNA polymerase II. Alternatively, a native B. anthracis promoter can be used to direct transcription of the nucleic acid molecule, using, for example, a B. anthracis RNA polymerase enzyme. In addition, operably linked can refer to an appropriate connection between the nucleic acid molecule and a heterologous coding sequence, such as a reporter gene, in such a way as to permit expression of the heterologous coding sequence.

Constructs suitable for use in the methods of the invention typically include, in addition to B. anthracis capB, pagA or lef nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention can be propagated in a host cell. As used herein, "host cell" includes prokaryotes and eukaryotes, such as yeast, plant and animal cells. Prokaryotic hosts may include E. coli, Salmonella spp., Serratia spp. and Bacillus spp. Eukaryotic hosts include yeasts such as S. cerevisiae, S. pombe, Pichia pastoris, mammalian cells such as COS cells or Chinese hamster ovary (CHO) cells, insect cells, and plant cells such as Arabidopsis thaliana and Nicotiana tabacum. Other host cells known in the art may be used according to the present invention.

A construct of the invention can be introduced into a host cell using any of the techniques known to those of ordinary skill in the art, such as calcium phosphate precipitation, electroporation, heat shock, lipofection, microinjection, and viral-mediated nucleic acid transfer. In addition, naked DNA can be delivered directly to cells using methods known in the art. See e.g., U.S. Pat. Nos. 5,580,859 and 5,589,466, which are herein incorporated by reference.

Polymerase chain reaction (PCR) methods known in the art may be used according to the present invention. See e.g., U.S. Pat. Nos. 4,683,202, 4,683,195, 4,800,159, and 4,965,188, which are herein incorporated by reference. PCR methods known in the art may be used to detect, measure, or monitor B. anthracis in a sample. In preferred embodiments, real-time PCR methods are used according to the present invention to detect, measure, or monitor B. anthracis in a sample. See e.g., WO 97/46707, WO 97/46714 and WO 97/46712, which are herein incorporated by reference.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined.

Within each thermocycler run, control samples are cycled as well. Positive control samples can amplify a B. anthracis nucleic acid control template using, for example, control primers and control probes. Positive control samples can also amplify, for example, a plasmid construct containing a B. anthracis nucleic acid molecule. Such a plasmid control can be amplified internally (e.g., within the sample) or in a separate sample run side-by-side with a test sample. Each thermocycler run should also include a negative control that, for example, lacks B. anthracis template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

The nucleic acid molecules of the present invention may be used with fluorescence resonance energy transfer (FRET), Scorpions, and Molecular Beacons assays. See Szollosi, et al. (1998) Cytometry 34(4):159-179; Schweitzer and Kingsmore (2001) Curr. Opin. Biotechnol. 12(1):21-27; and Antony and Subramaniam (2001) J. Biomol. Struct. Dyn. 19(3):497-504, which are herein incorporated by reference.

Fluorescence Resonance Energy Transfer (FRET) methods known in the art may also be used according to the present invention. See e.g., U.S. Pat. Nos. 4,996,143, 5,565,322, 5,849,489, and 6,162,603, which are herein incorporated by reference. As described herein, amplification products can be detected using labeled hybridization probes that take advantage of FRET technology. A common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by a light source. During FRET, the fluorescein transfers its energy to an acceptor fluorescent moiety such as LightCycler™-Red 640 (LC™-Red 640) or LightCycler™-Red 705 (LC™-Red 705). The acceptor fluorescent moiety then emits light of a longer wavelength, which is detected by an optical detection system such as the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of B. anthracis genomes).

Another FRET format utilizes TaqMan® technology to detect the presence or absence of an amplification product, and hence, the presence or absence of B. anthracis. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TaqMan® technology, and is suitable for performing the methods described herein for detecting B. anthracis. Information on PCR amplification and detection using an ABI PRISM® 770 system is known in the art.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

PCR methods known in the art may be used in conjunction with FRET technology. In some embodiments, a LightCycler™ instrument or the like is used. The specifications of the LightCycler™ System, methods of using and real-time and on-line monitoring of PCR are known in the art. See WO 97/46707, WO 97/46714 and WO 97/46712, which are herein incorporated by reference.

As an alternative to FRET, an amplification product can be detected using a double-stranded DNA binding dye such as a fluorescent DNA binding dye (e.g., SYBRGreenI® or SYBRGold® (Molecular Probes, Eugene, Oreg.)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

In some embodiments, the methods of the invention include steps to avoid contamination. For example, an enzymatic method utilizing uracil-DNA glycosylase is described in U.S. Pat. Nos. 5,035,996, 5,683,896 and 5,945,313, which are herein incorporated by reference, to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

The nucleic acid molecules of the present invention may be multiplexed or used in conjunction with other assays for the detection of a Bacillus anthracis based on the presence of at least one nucleic acid molecule of the present invention. The nucleic acid molecules of the present invention may be multiplexed or used in conjunction with other assays for the detection of organisms in addition to B. anthracis based on the presence of at least one nucleic acid molecule that is unique to the given organism. For example, the nucleic acid molecules of the present invention may be used in conjunction with assays, known in the art, for organisms belonging to Bacillus, Mycobacterium, Francisella, Brucella, Clostridium, Yersinia, Variola, Orthopox, and Burkholderia. See e.g. Fasanella, A. et al. (2003) J. Clin. Microbiol. 41(2):896-899 (Bacillus anthracis); Drago, L. et al. (2002) J. Clin. Microbiol. 40(11):4399 (Bacillus anthracis); Espy, M. J. et al. (2002) Mayo Clin. Proc. 77(7):624-628 (bioterrorism agents); Montenegro, S. H. et al. (2003) Clin. Infect. Dis. 36(1):16-23 (Mycobacterium tuberculosis); Johansson, A. et al. (2000) J. Clin. Microbiol. 38(11):4180-4185 (Francisella tularensis); Emanuel, P. A. et al. (2003) J. Clin. Microbiol. 41(2):689-693 (Francisella tularensis); Navarro, E. et al. (2002) FEMS Immunol. Med. Microbiol. 34(2):147-151 (Brucella spp); Bricker, B. J. (2002) Vet. Microbiol. 90(1-4):435-446 (Brucella); Lindstrom, M. et al. (2001) Appl. Environ. Microbiol. 67(12):5694-5699 (Clostridium botulinum); Lindler, L. E. et al. (2001) J. Clin. Microbiol. 39(10):3649-3655 (Yersinia pestis); Radnedge, L. et al. (2001) Appl. Environ. Microbiol. 67(8):3759-3762 (Yersinia pestis); Czerny, C. P. et al. (1997) Arch. Virol. Suppl. 13:13-24 (orthopox virus); Espy, M. J. et al. (2002) J. Clin. Microbiol. 40(6):1985-1988 (smallpox); Meyer, H. et al. (2002) J. Vet. Med. B. Infect. Dis. Vet. Public Health 49(1):17-19 (variola); Meyer, H. et al. (1997) J. Virol. Methods 64(2):217-221 (orthopox); Woo, P. C. et al. (2002) Diagn. Microbiol. Infect. Dis. 44(2): 143-149 (Burkholderia); and Vermis, K. et al. (2002) J. Med. Microbiol. 51(11):937-940 (Burkholderia), which are herein incorporated by reference.

Methods of the invention also can be used for B. anthracis vaccine efficacy studies or epidemiology studies. For example, an attenuated B. anthracis in an anthrax vaccine can be detected using the methods of the invention during the time when bacteria is still present in an individual. For such vaccine efficacy studies, the methods of the invention can be used to determine, for example, the persistence of an attenuated strain of B. anthracis used in a vaccine, or can be performed in conjunction with an additional assay such as a serologic assay to monitor an individual's immune response to such a vaccine. In addition, methods of the invention can be used to distinguish one B. anthracis strain from another for epidemiology studies of, for example, the origin or severity of an outbreak of B. anthracis.

Representative biological samples that can be used in practicing the methods of the invention include dermal swabs, cerebrospinal fluid, blood, sputum, bronchio-alveolar lavage, bronchial aspirates, lung tissue, and feces. Collection and storage methods of biological samples are known to those of skill in the art. Biological samples can be processed (e.g., by nucleic acid extraction methods and/or kits known in the art) to release *B. anthracis* nucleic acid or in some cases, the biological sample can be contacted directly with the PCR reaction components and the appropriate oligonucleotides.

Non-biological samples such as air samples, powders, and surface swipes and rinse products from suspicious materials also can be examined for the detection of *B. anthracis*. For example, a powder can be dissolved in a solvent such as water, and the methods of the invention can be performed on varying dilutions (e.g., 1:10, 1:100, or 1:1000) of the resulting solution. A solvent can be added to a collection vial of an air sample collection device and assayed using methods of the invention, or alternatively, a filter on an air sample collection device can be rinsed and assayed. In addition, a solid material (e.g., paper) can be swiped or rinsed for the purpose of detecting *B. anthracis*, and a non-turbid solution produced. Dilutions of such a surface swipe or rinse can be used in a real-time amplification reaction of the invention.

Biological or non-biological samples can be cultured in a medium suitable for growth of *B. anthracis*. The culture media then can be assayed for the presence or absence of *B. anthracis* using the methods of the invention as described herein. For example, samples arriving at a clinical laboratory for detection of *B. anthracis* using the methods of the invention can be in the form of a liquid culture that had been inoculated with a biological sample from an individual or with a non-biological sample.

The present invention further provides kits for use with nucleic acid hybridization assays such as PCR amplification and PCR assays, including TaqMan® based assays, fluorescence resonance energy transfer (FRET), Scorpions, and Molecular Beacons assays. See Szollosi, et al. (1998) Cytometry 34(4):159-179; Schweitzer and Kingsmore (2001) Curr. Opin. Biotechnol. 12(1):21-27; and Antony and Subramaniam (2001) J. Biomol. Struct. Dyn. 19(3):497-504, which are herein incorporated by reference. Such kits comprise the IPC nucleic acid molecule and one or more components necessary for performing the assay. Components may be compounds, reagents, containers, instructions and/or equipment.

The kits may be used for any one or more of the uses described herein, and, accordingly, may contain instructions (written and/or electronic) for any one or more of the following uses: determining whether a target nucleic acid sequence is present in a sample, detecting a target nucleic acid sequence, quantifying a target nucleic acid sequence, comparing target nucleic acid sequence to a reference sequence, determining genotype, determining allele composition of a target nucleic acid, detecting and/or quantifying multiple nucleic acid sequences, and use of the methods in conjunction with nucleic acid amplification techniques.

The kits of the invention comprise one or more containers comprising any combination of the components or reagents described herein. For example, in one embodiment, the kit comprises the nucleic acid molecules of the present invention and a set of primers and probes for conducting an assay for a target nucleic acid molecule. The kit may further include at least one label and at least one substrate or for producing a signal. The kit may further include deoxynucleoside triphosphates and/or ribonucleoside triphosphates. The kit may further include one or more suitable buffers for conducting the given assay. Each component of the kit can be packaged in separate containers or some components can be combined in one container where cross-reactivity and shelf life permit. The kits of the present invention may also include an internal positive control (IPC) for use in nucleic acid hybridization assays including probe-based nucleic acid assays such as TaqMan® based assays.

As used herein, "sequence identity" in the context of two or more nucleic acid molecules, refers to two or more sequences or subsequences that are the same or have a specified percentage of nucleotide bases that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. The percentage of sequence identity may be calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Methods of alignment of sequences for comparison are well-known in the art. See e.g Smith & Waterman (1981) Adv. Appl. Math. 2:482; Needleman & Wunsch (1970) J. Mol. Biol. 48:443; and Pearson & Lipman (1988) PNAS USA 85:2444, which are herein incorporated by reference. Alignment may be conducted using computer programs such as GAP, BESTFIT, FASTA, and TFASTA in the Wisconsin Genetics Software Package (Genetics Computer Group, 575 Science Dr., Madison, Wis.), or manually by visual inspection. See also Feng & Doolittle (1987) J. Mol. Evol. 35:351-360; Higgins & Sharp (1989) CABIOS 5:151-153; and Devereaux et al. (1984) Nuc. Acids Res. 12:387-395, which are herein incorporated by reference.

Alternatively, BLAST and BLAST 2.0 algorithms may be used to determine the sequence identity of two or more sequences. See Altschul et al. (1977) Nuc. Acids Res. 25:3389-3402 and Altschul et al. (1990) J. Mol. Biol. 215:403-410, which are herein incorporated by reference. BLAST analyses are publicly available through the National Center for Biotechnology Information at the World Wide Web at ncbi.nlm.nih.gov/.

As provided herein, the nucleic acid molecules of the present invention include nucleic acid molecules that have at least about 70% identity, preferably about 80% identity or more, more preferably about 90% identity or more, more preferably about 95% identity or more, even more preferably about 98% identity or more, over the 106 bp region set forth in SEQ ID NO:1. Nucleic acid molecules that have sequences that have at least about 90% identity to SEQ ID NO:1 are "substantially identical" to SEQ ID NO:1.

As used herein, the phrase "selectively (or specifically) hybridizes to" refers to the binding, duplexing, or hybridizing of a nucleic acid molecule to a particular nucleotide sequence only in a sample comprising other nucleic acid molecules under stringent hybridization to moderate hybridization conditions. For selective or specific hybridization, a positive signal is at least about 2 times, preferably about 5 times, more preferably about 10 times the background hybridization. Stringent hybridization conditions are about 5° C. below the thermal melting temperature (Tm) of the probe to about 10° C. below Tm. Moderate hybridization conditions are about 10° C. below the thermal melting temperature (Tm) of the probe to about 20° C. to about 25° C. below Tm.

The following examples are intended to illustrate but not to limit the invention.

EXAMPLE 1

A. Nucleic Acid Isolation

Delta ANR-SWS *B. anthracis* (dANR) and *B. cereus* ATCC 21769 (BACI177) were extracted using the QIAamp DNA mini kits (Qiagen, Valencia, Calif.). An overnight culture of cells were pelleted by centrifugation for 10 minutes at 5000×g and resuspended in 180 µl of Dulbecco's phosphate buffered saline (Gibco BRL, Rockville, Md.). Next, 20 µl of proteinase K (Qiagen) and 100 µl of 4 mg/ml RNAse A (Promega, Madison, Wis.) were added to the cell suspension and incubated at room temperature for 15 minutes. A 200 µl volume of AL buffer (Qiagen, Valencia, Calif.) was added to the above tubes, mixed, and then incubated at 55° C. for 1 hour. Then, 210 µl of 100% ethanol was added to the lysed cells and vortexed. This mixture was transferred to a QIAamp spin column in a collection tube and centrifuged at 6,000×g for 2 minutes. The spin column was transferred to a new collection tube, 500 µl of AW1 (Qiagen, Valencia, Calif.) buffer were added to the spin column and centrifuged at 6,000 ×g for 2 minutes. The spin column was transferred to another new collection tube, 500 µl of AW2 (Qiagen, Valencia, Calif.) buffer were added, and the tubes were centrifuged at 6,000×g for 2 minutes. The spin column was then transferred to a 1.5 ml eppendorf tube, 50 µl of preheated 70° C. AE buffer (Qiagen, Valencia, Calif.) were added to the spin column, and the tubes were incubated at 70° C. for 5 minutes. The spin column and eppendorf tube were spun at 6,000×g for 1 minute to elute the DNA. To assess the quality of the DNA prior to the subtraction, 2 µl of each DNA sample was analyzed by gel electrophoresis using a 1% agarose gel run at 90 volts for 65 minutes.

B. Bacterial Subtraction

The Clontech PCR-Select™ Bacterial Genome Subtraction Kit (Clontech, Palo Alto, Calif.) was used to identify sequences unique to *B. anthracis*. BACI177 was chosen for the driver DNA and dANR was chosen to be the tester. Genomic *Escherichia coli* provided in the kit was used as a control. The majority of the subtraction-hybridization was performed according to the manufacturer's instructions with the modifications described below. Restriction enzyme digests were performed according to the manufacturer's instructions and the digest was analyzed for efficiency by gel electrophoresis as described herein. The digested nucleic acid was purified and adaptor ligations were performed on the tester and control DNA. Ligation efficiency analysis was performed by PCR with the following components: 35.5 µl of molecular biology grade (MBG) $H_2O$, 2 µl of 10 mM dNTP mix (Roche, Indianapolis, Ind.), 5 µl of 10×PCR buffer, 4 µl of 25 mM $MgCl_2$, 0.5 µl of AmpliTaq Gold (Applied Biosystems, Foster City, Calif.), 1 µl of each primer, and 1 µl ligated DNA per 50 µl reaction. The primers used with the tester DNA were

```
704F: 5'AGATTTTCCGACGGCACGTT3'   (SEQ ID NO:90)
``` at a concentration of 50 pmol/µl and

```
829R: 5'TTTCAATCAATCGCGCCTTATT3'   (SEQ ID NO:91)
``` at a concentration of 50 pmol/µl, spanning a region of the gyrA gene in *B. anthracis*.

One tester DNA reaction incorporated primer 704F with PCR primer 1 at a concentration of 0.2 µM/µl, while primer 704F and primer 829R were used in the other tester DNA reactions. The PCR reaction conditions were 72° C. for 2 minutes, 95° C. for 10 minutes, followed by 35 cycles of 95° C. for 2 minutes, 60° C. for 1 minute, 72° C. for 1 minute with a final extension at 72° C. for 10 minutes using a MJ Research PTC-100 Thermal Cycler (Waltham, Mass.). The DNA products were analyzed by gel electrophoresis using a 2% gel run at 150 volts for 30 minutes. Following the ligation efficiency analysis, the two hybridization steps were performed at an incubation temperature of 62° C. for both the tester and driver DNA due to their lower GC content. The PCR reactions to amplify tester nucleic acid followed the manufacturer's instructions with the exception of the nested PCR running for 17 cycles, and were performed on a MJ Research PTC-100 Thermal Cycler. The DNA products were analyzed by gel electrophoresis as described above.

C. Bacterial Cloning

The subtracted dANR nested PCR products were cloned into the pCR®2.1-TOPO® vector using the TOPO TA Cloning® kit (Invitrogen, Carlsbad, Calif.) according to the manufacturer's instructions for chemical transformation. White colonies were selected and boiled in 50 µl of $H_2O$ for 10 minutes to break up the cells and release nucleic acid. PCR was performed using the following components per 100 µl reaction: 71 µl of MBG $H_2O$, 4 µl of 10 mM dNTP mix, 10 µl of 10×PCR Buffer, 8 µl of 25 mM $MgCl_2$, 1 µl of AmpliTaq Gold, 2 µl of 50 pmol/µl M13 forward primer (Invitrogen), 2 µl of 50 pmol/µl M13 reverse primer (Invitrogen), and 2 µl of supernatant from the boil preparation. PCR reaction conditions were 72° C. for 2 minutes, 95° C. for 10 minutes, followed by 30 cycles of 95° C. for 2 minutes, 55° C. for 1 minute, 72° C. for 1 minute with a final extension at 72° C. for 10 minutes using a MJ Research PTC-100 Thermal Cycler. PCR products were analyzed using gel electrophoresis as described herein. Clones with positive inserts were selected for sequencing and further analysis.

D. Bacterial Sequencing

PCR products from the selected clones were purified using the Montage $PCR_{96}$ Cleanup Kit (Millipore, Billerica, Mass.). Sequencing reactions were carried out using 8 µl Big Dye (Applied Biosystems), 1 µl of 50 pmol/µl M13 forward primer or 1 µl 50 pmol/µl M13 reverse primer (Invitrogen), 1 µl of purified PCR product, and 10 µl of MBG $H_2O$. The sequencing reactions were cycled on a MJ PTC-100 Thermal Cycler at 85° C. for 30 seconds, followed by 25 cycles of 96° C. for 10 seconds, 50° C. for 5 seconds, and 60° C. for 4 minutes with a final extension at 60° C. for 10 minutes. Sequencing was performed on an ABI 3100 (Applied Biosystems) and aligned using DNASTAR software (DNASTAR, Inc., Madison, Wis.). BLAST searches were submitted for all sequences to eliminate regions not unique to *B. anthracis* and those with possible cross-reactivity with other organisms. A single clone (B26) was picked for further analysis.

FIG. 1 shows the results of subtraction after nested PCR, representing bands present in unsubtracted dANR that do not occur in subtracted dANR. A prominent band of about 1000 bp existed in the subtracted dANR lane. The entire PCR product from subtracted dANR was cloned and analyzed by PCR using M13 primers. These primer sequences flank the inserted region of the PCR product on the pCR®2.1-TOPO® vector. Four clones generated a PCR product with an insert of about 1000 bp, were sequenced, and determined to be unique. All BLAST searches exhibited low bit scores and E values, but clone B26 presented the least amount of homologous hits, therefore it was selected for continued testing.

EXAMPLE 2

Primer and Probe Design and Testing

Prospective primers and probes were generated using Primer Express software version 2.0 (Applied Biosystems) and the imported sequence from clone B26. Primers were further analyzed for palindromes, hairpins, dimer formation, and annealing temperature with NetPrimer (BioSoft International, Palo Alto, Calif.).

A. Primer Testing Using Standard PCR

Two forward primers and two reverse primers were assessed using standard PCR on MJ Research PTC-100 Thermal Cycler with the following components per 20 μl reaction: 10.44 μl of MBG H$_2$O, 2 μl of 10×2 mM dNTPs (Idaho Technology, Salt Lake City, Utah), 2 μl of 10×PCR buffer containing 50 mM MgCl$_2$ (Idaho Technology), 0.2 μl of 50 pmol/μl forward primer, 0.2 μl of 50 pmol/μl reverse primer, 0.16 μl of 5 units/μl of Platinum Taq (Invitrogen, Grand Island, N.Y.), and 5 μl of *Bacillus* species DNA either at 1 ng/μl or 100 pg/μl. Reactions cycled at 94° C. for 2 minutes, followed by 34 cycles of 94° C. for 30 seconds, 60° C. for 30 minutes, and 72° C. for 1 minute with a final extension at 72° C. for 10 minutes on a MJ Research PTC-100 Thermal Cycler. Reactions were analyzed by gel electrophoresis as described herein. Primers

```
                                              (SEQ ID NO:2)
F41: 5'TGGCGGAAAAGCTAATATAGTAAAGTA3'
and R146: the reverse complement of SEQ ID NO:3
``` were selected for further testing. Forty-two *B. anthracis* and 53 *Bacillus* species were tested according to the PCR conditions defined above. Reactions were analyzed by gel electrophoresis as described herein.

Primers were designed from a portion of the B26 sequence. Initial testing was performed with two forward and two reverse primers in four different combinations. All combinations amplified, but the primer combination F41 and R146 generated the largest amount of DNA and was selected to test 42 *B. anthracis* and 53 *Bacillus* species, given in Table 2 as follows:

TABLE 2

List of *Bacillus* species used for initial Standard PCR testing

| Organism | Strain | ATCC |
|---|---|---|
| Bacillus anthracis | CDC 607 | |
| Bacillus anthracis | CDC 471 | |
| Bacillus anthracis | V770-NP-1R | |
| Bacillus anthracis | Delta-NH-1 | |
| Bacillus anthracis | ST1 | |
| Bacillus anthracis | Delta-Ames-1 | |
| Bacillus anthracis | NH | |
| Bacillus anthracis | Vollum | |
| Bacillus anthracis | Vollum 1 | |
| Bacillus anthracis | Vollum 1B | |
| Bacillus anthracis | English Vollum | |
| Bacillus anthraces | AMES | |
| Bacillus anthracis | Buffalo | |
| Bacillus anthracis | NH | |

TABLE 2-continued

List of *Bacillus* species used for initial Standard PCR testing

| Organism | Strain | ATCC |
|---|---|---|
| Bacillus anthracis | 4229 | |
| Bacillus anthracis | V770-2P | |
| Bacillus anthracis | FLA-V770 | |
| Bacillus anthracis | V770 | |
| Bacillus anthracis | 108 | |
| Bacillus anthracis | 205 | |
| Bacillus anthracis | 57 | |
| Bacillus anthracis | N994 | |
| Bacillus anthracis | SK-465 | |
| Bacillus anthracis | SK-102 | |
| Bacillus anthracis | SK-162 | |
| Bacillus anthracis | SK-61 | |
| Bacillus anthracis | SK-128 | |
| Bacillus anthracis | N-99 | |
| Bacillus anthracis | ST-15 | |
| Bacillus anthracis | 183 | |
| Bacillus anthracis | Ger. LVS | |
| Bacillus anthracis | SK-31 | |
| Bacillus anthracis | M | |
| Bacillus anthracis | G-28 | |
| Bacillus anthracis | Sterne, (British) | |
| Bacillus anthracis | 1928 | |
| Bacillus anthracis | SPS 97.13.079 | |
| Bacillus anthracis | Delta-ANR-SWS | |
| Bacillus anthracis | 4728 | |
| Bacillus anthraces | SPS 97.13.213 | |
| Bacillus anthraces | Delta Sterne | |
| Bacillus anthracis | Arkansas | |
| Bacillus cereus | | 7039 |
| Bacillus cereus | | 12480 |
| Bacillus cereus | | 13472 |
| Bacillus cereus | | 13824 |
| Bacillus cereus | | 14603 |
| Bacillus cereus | | 14893 |
| Bacillus cereus | | 15816 |
| Bacillus cereus | | 19625 |
| Bacillus cereus | | 19637 |
| Bacillus cereus | | 21182 |
| Bacillus cereus | | 21366 |
| Bacillus cereus | | 21634 |
| Bacillus cereus | | 21768 |
| Bacillus cereus | | 21769 |
| Bacillus cereus | | 21770 |
| Bacillus cereus | | 21771 |
| Bacillus cereus | | 21772 |
| Bacillus cereus | | 21928 |
| Bacillus cereus | | 25621 |
| Bacillus cereus | | 27348 |
| Bacillus cereus | | 27522 |
| Bacillus cereus | | 27877 |
| Bacillus cereus | | 31293 |
| Bacillus cereus | | 31429 |
| Bacillus cereus | | 31430 |
| Bacillus cereus | | 33018 |
| Bacillus cereus | | 33019 |
| Bacillus cereus | | 43881 |
| Bacillus cereus | | 53522 |
| Bacillus cereus | | 55055 |
| Bacillus cereus | | 700282 |
| Bacillus cereus | | 10792 |
| Bacillus cereus | | 9139 |
| Bacillus cereus | | 9818 |
| Bacillus cereus | | 10876 |
| Bacillus cereus | | 13061 |
| Bacillus thuringiensis | | 13366 |
| Bacillus thuringiensis | | 13367 |
| Bacillus thuringiensis | | 19266 |
| Bacillus thuringiensis | | 19267 |
| Bacillus thuringiensis | | 19268 |
| Bacillus thuringiensis | | 19269 |
| Bacillus thuringiensis | | 19270 |
| Bacillus thuringiensis | | 29730 |
| Bacillus thuringiensis | | 33679 |
| Bacillus thuringiensis | | 35646 |
| Bacillus thuringiensis | | 39152 |

TABLE 2-continued

List of *Bacillus* species used for initial Standard PCR testing

| Organism | Strain | ATCC |
|---|---|---|
| *Bacillus thuringiensis* | | NA |
| *Bacillus popilliae* | | 14706 |
| *Bacillus coagulans* | | 7050 |
| *Bacillus subtilis* var *niger* | | 9372 |
| *Bacillus subtilis* var *niger* | | NA |
| *Bacillus macerans* | | 8244 |

All 42 *B. anthracis* isolates produced an amplicon of about 100 bp. In contrast, the *Bacillus* species tested did not show any product except for *B. cereus* ATCC 21771 (BACI179) that generated a very faint band at 1000 bp (data not shown).

B. Probe Testing Using Real-Time PCR

Two Taqman® Minor Groove Binder (MGB) probes were tested using real-time PCR on the Ruggedized Advanced Pathogen Identification Device (RAPID) (Idaho Technology) with primers F41 and R146. Background fluorescence of the probes was obtained by diluting the 100 μM MGB Taqman® probes to 1 μM so that fluorescence was between 10-20 with a gain setting of 16. The probes were tested against 16 *B. anthracis* and 13 *B. cereus*. The master mix contained 8.44 μl of MBG $H_2O$, 2 μl of 10×2 mM dNTPs, 2 μl of 10× PCR buffer containing 50 mM $MgCl_2$, 0.2 μl of 50 pmol/μl F41 primer, 0.2 μl of 50 pmol/μl R146 primer, 2 μl of 1 mM probe, 0.16 μl of 5 units/μl of Platinum Taq, and 5 μl of 1 ng/μl of DNA per 20 μl reaction. The PCR cycling conditions for all RAPID runs were 94° C. for 2 minutes followed by 45 cycles of 94° C. for 20 seconds and 60° C. for 20 seconds. Probe BALB26588-MGB (P88)

```
5'ACTTCTAAAAAGCAGATAGAAAT3' (SEQ ID NO:4)
``` was chosen for optimization on the RAPID. Five concentrations of $MgCl_2$ (3 mM, 4 mM, 5 mM, 6 mM, 7 mM) and ten concentrations of primers F41 and R146 (0.1 μM, 0.2 μM, 0.3 μM, 0.4 μM, 0.5 μM, 0.6 μM, 0.7 μM, 0.8 μM, 0.9 μM, 1.0 μM) were tested in triplicate using 1 pg of *B. anthracis* Ames DNA. The combination that exhibited the earliest crossing threshold (CT) and highest end fluorescence (Ef) was chosen as the optimal condition (5 mM $MgCl_2$, 0.7 μM for each primer). The optimized master mix contained 8.28 μl of $H_2O$, 2 μl of 10×2 mM dNTPs, 2 μl of 10×PCR buffer containing 50 mM $MgCl_2$, 0.28 μl of 50 pmol/μl F41 primer, 0.28 μl of 50 pmol/μl R146 primer, 2 μl of 1 mM P88 probe, and 0.16 μl of 5 units/μl Platinum Taq per 20 μl reaction. Ten-fold dilutions of Ames DNA were made from 4 pg/μl to 0.4 fg/μl so that 2.5 μl of each dilution along with 2.5 μl of human DNA (5 ng) or 2.5 μl of $H_2O$ could be added to 15 μl of optimized master mix.

After primers were tested and selected using standard PCR, two probes previously designed with the primers were tested against 16 *B. anthracis* and 13 *B. cereus* strains with the RAPID. Table 3 provides a list of the *Bacillus* species tested:

TABLE 3

List of *Bacillus* species used for the sensitivity and specificity testing of the real-time chromosomal PCR assay

| Organism | Strain | ATCC | PA | Cap |
|---|---|---|---|---|
| *Bacillus anthracis* | CDC 471 | | NEG | NEG |
| *Bacillus anthracis* | Delta-UM23-1-1 | | NEG | NEG |
| *Bacillus anthracis* | 183 | | NEG | NEG |
| *Bacillus anthracis* | Delta-ANR-SWS | | NEG | NEG |
| *Bacillus anthracis* | Delta Sterne | | NEG | NEG |
| *Bacillus anthracis* | Delta-NH-1 | | NEG | POS |
| *Bacillus anthracis* | 4229 | | NEG | POS |
| *Bacillus anthracis* | 1928 | | NEG | POS |
| *Bacillus anthracis* | 4728 | | NEG | POS |
| *Bacillus anthracis* | 107 | | NEG | POS |
| *Bacillus anthracis* | V770-NP-1R | | POS | NEG |
| *Bacillus anthracis* | ST1 | | POS | NEG |
| *Bacillus anthracis* | Arkansas | | POS | NEG |
| *Bacillus anthracis* | SK-465 | | POS | NEG |
| *Bacillus anthracis* | SK-102 | | POS | NEG |
| *Bacillus anthracis* | SK-61 | | POS | NEG |
| *Bacillus anthracis* | ST-15 | | POS | NEG |
| *Bacillus anthracis* | Ger. LVS | | POS | NEG |
| *Bacillus anthracis* | M | | POS | NEG |
| *Bacillus anthracis* | Sterne, (British) | | POS | NEG |
| *Bacillus anthracis* | V770-NP1-R | | POS | NEG |
| *Bacillus anthracis* | SPS 97.13.213 | | POS | NEG |
| *Bacillus anthracis* | CDC 607 | | POS | POS |
| *Bacillus anthracis* | Delta-Ames-1 | | POS | POS |
| *Bacillus anthracis* | Vollum 1 | | POS | POS |
| *Bacillus anthracis* | Vollum 1B | | POS | POS |
| *Bacillus anthracis* | English Vollum | | POS | POS |
| *Bacillus anthracis* | Ames | | POS | POS |
| *Bacillus anthracis* | Buffalo | | POS | POS |
| *Bacillus anthracis* | NH | | POS | POS |
| *Bacillus anthracis* | V770-2P | | POS | POS |
| *Bacillus anthracis* | FLA-V770 | | POS | POS |
| *Bacillus anthracis* | V770 | | POS | POS |
| *Bacillus anthracis* | 108 | | POS | POS |
| *Bacillus anthracis* | 205 | | POS | POS |
| *Bacillus anthracis* | 57 | | POS | POS |
| *Bacillus anthracis* | N994 | | POS | POS |
| *Bacillus anthracis* | SK-162 | | POS | POS |
| *Bacillus anthracis* | SK-128 | | POS | POS |
| *Bacillus anthracis* | N-99 | | POS | POS |
| *Bacillus anthracis* | SK-31 | | POS | POS |
| *Bacillus anthracis* | G-28 | | POS | POS |
| *Bacillus anthracis* | SPS 97.13.079 | | POS | POS |
| *Bacillus anthracis* | NH | | POS | POS |
| *Bacillus anthracis* | Vollum | | POS | POS |
| *Bacillus cereus* | | 7039 | NEG | NEG |
| *Bacillus cereus* | | 12480 | NEG | NEG |
| *Bacillus cereus* | | 13472 | NEG | NEG |
| *Bacillus cereus* | | 13824 | NEG | NEG |
| *Bacillus cereus* | | 14603 | NEG | NEG |
| *Bacillus cereus* | | 14893 | NEG | NEG |
| *Bacillus cereus* | | 15816 | NEG | NEG |
| *Bacillus cereus* | | 19625 | NEG | NEG |
| *Bacillus cereus* | | 19637 | NEG | NEG |
| *Bacillus cereus* | | 21182 | NEG | NEG |
| *Bacillus cereus* | | 21366 | NEG | NEG |
| *Bacillus cereus* | | 21634 | NEG | NEG |
| *Bacillus cereus* | | 21768 | NEG | NEG |
| *Bacillus cereus* | | 21769 | NEG | NEG |
| *Bacillus cereus* | | 21770 | NEG | NEG |
| *Bacillus cereus* | | 21771 | NEG | NEG |
| *Bacillus cereus* | | 21772 | NEG | NEG |
| *Bacillus cereus* | | 21928 | NEG | NEG |
| *Bacillus cereus* | | 25621 | NEG | NEG |
| *Bacillus cereus* | | 27348 | NEG | NEG |
| *Bacillus cereus* | | 27522 | NEG | NEG |
| *Bacillus cereus* | | 27877 | NEG | NEG |
| *Bacillus cereus* | | 31293 | NEG | NEG |
| *Bacillus cereus* | | 31429 | NEG | NEG |
| *Bacillus cereus* | | 31430 | NEG | NEG |
| *Bacillus cereus* | | 33018 | NEG | NEG |
| *Bacillus cereus* | | 33019 | NEG | NEG |
| *Bacillus cereus* | | 43881 | NEG | NEG |
| *Bacillus cereus* | | 53522 | NEG | NEG |

TABLE 3-continued

List of Bacillus species used for the sensitivity and specificity testing of the real-time chromosomal PCR assay

| Organism | Strain | ATCC | PA | Cap |
|---|---|---|---|---|
| Bacillus cereus | | 55055 | NEG | NEG |
| Bacillus cereus | | 700282 | NEG | NEG |
| Bacillus cereus | | 9139 | NEG | NEG |
| Bacillus cereus | | 9818 | NEG | NEG |
| Bacillus cereus | | 10876 | NEG | NEG |
| Bacillus cereus | | 13061 | NEG | NEG |
| Bacillus cereus | | 10987 | NEG | NEG |
| Bacillus thuringiensis | | 10792 | NEG | NEG |
| Bacillus thuringiensis | | 13366 | NEG | NEG |
| Bacillus thuringiensis | | 13367 | NEG | NEG |
| Bacillus thuringiensis | | 19266 | NEG | NEG |
| Bacillus thuringiensis | | 19267 | NEG | NEG |
| Bacillus thuringiensis | | 19268 | NEG | NEG |
| Bacillus thuringiensis | | 19269 | NEG | NEG |
| Bacillus thuringiensis | | 19270 | NEG | NEG |
| Bacillus thuringiensis | | 29730 | NEG | NEG |
| Bacillus thuringiensis | | 33679 | NEG | NEG |
| Bacillus thuringiensis | | 39152 | NEG | NEG |
| Bacillus thuringiensis | | 35646 | NEG | NEG |
| Bacillus thuringiensis | | NA | NEG | NEG |
| Bacillus subtilis | | 6633 | NEG | NEG |
| Bacillus subtilis var niger | | NA | NEG | NEG |
| Bacillus subtilis var niger | | 9372 | NEG | NEG |
| Bacillus macerans | | 8244 | NEG | NEG |
| Bacillus stearothermophilus | | 7953 | NEG | NEG |
| Bacillus popilliae | | 14706 | NEG | NEG |
| Bacillus coagulans | | 7050 | NEG | NEG |
| Bacillus licheniformis | | 12759 | NEG | NEG |
| Bacillus halodurans | | 21591D | NEG | NEG |
| Bacillus brevis | | 8246 | NEG | NEG |
| Bacillus mycoides | | 31101 | NEG | NEG |
| Bacillus mycoides | | 21929 | NEG | NEG |
| Bacillus species | 813+ #11 | | NEG | NEG |

Specificity and sensitivity were 100% for each probe when tested. Positive and negative reactions may be readily determined by those skilled in the art. Both probes generated similar CT values for the samples tested, but P88 generated a higher Ef for the samples tested, so it was chosen for optimization. After optimization of MgCl$_2$ and primer concentration, serial ten-fold dilutions made with Ames DNA gave positive triplicate results to 1 fg. When the reactions were spiked with 5 ng of human DNA, positive triplicate results to 1 fg were still obtained with no observed changes in CT or Ef.

C. Cross-Reactivity

Cross-reactivity and other Bacillus species testing using the real-time optimized conditions. A panel of 77 organisms was run using the optimized conditions to test for cross-reactivity. Master mix with 5 μl of 20 pg/μl DNA isolated from each organism was used. Sensitivity and specificity testing was also accomplished as described above using 45 *Bacillus anthracis* strains and 62 *Bacillus* species. Table 4 provides a list of organisms used to test cross-reactivity with the real-time chromosomal PCR assay:

TABLE 4

List of organisms used to test cross-reactivity with the real-time chromosomal PCR assay

| Organism | ATCC # |
|---|---|
| *Acinetobacter baumanni* | 19606 |
| *Alcaligenes xylosoxydans* | 27061 |
| *Bacillus anthracis* Delta Sterne | NA |
| *Bacillus anthracis* 4728 | |
| *Bacillus anthracis* Delta-NH-1 | NA |
| *Bacillus anthracis* ST1 | NA |
| *Bacillus anthracis* NH | NA |
| *Bacillus anthracis* Vollum | NA |
| *Bacillus anthracis* SPS 97.13.079 | NA |
| *Bacillus anthracis* Ames | NA |
| *Bacillus anthracis* V770-NP-1R | NA |
| *Bacillus anthracis* SPS 97.13.213 | NA |
| *Bacillus anthracis* Sterne | NA |
| *Bacillus cereus* | 10876 |
| *Bacillus cereus* | 13061 |
| *Bacillus coagulans* | 7050 |
| *Bacillus licheniformis* | 12759 |
| *Bacillus macerans* (*Paenibacillus macerans*) | 8244 |
| *Bacillus megaterium* | NA |
| *Bacillus polymyxa* | 842 |
| *Bacillus popilliae* | 14706 |
| *Bacillus sphaericus* | 4525 |
| *Bacillus staerothermophilus* | 7953 |
| *Bacillus subtilis* var. *niger* | NA |
| *Bacillus subtilis* var *niger* | 6633 |
| *Bacillus subtilis* var *niger* | 9372 |
| *Bacillus thuringiensis* | 39152 |
| *Bacillus thuringiensis* | 35646 |
| *Bacillus thuringiensis* | NA |
| *Bacteroides distasonis* | 8503 |
| *Bordetella bronchiseptica* | 10580 |
| *Budvicia aquatica* | 35567 |
| *Burkholderia cepacia* | 25416 |
| *Burkholderia pseudomallei* | NA |
| *Clostridium perfringens* | 13124 |
| *Clostridium sporogenes* | 3584 |
| *Comanonas acidovorans* | 15668 |
| *Enterococcus durans* | 6056 |
| *Enterococcus faecalis* | 29212 |
| *Enterococcus faecalis* | 700802D |
| *Escherichia coli* | 25922 |
| *Francisella tularensis* | NA |
| *Francisella tularensis* | NA |
| *Francisella tularensis* | NA |
| *Francisella tularensis* | NA |
| *Francisella tularensis* | NA |
| *Francisella tularensis* | NA |
| *Haemophilus influenzae* | 10211 |
| *Haemophilus influenzae* | 51907D |
| *Klebsiella pneumoniae* | 13883 |
| *Klebsiella pneumoniae* subsp. *pneumonioae* | 700721D |
| *Listeria monocytogenes* | 15313 |
| *Moraxella cattaharalis* | 25240 |
| *Neisseria lactamica* | 23970 |
| *Proteus mirabilis* | 7002 |
| *Proteus vulgaris* | 49132 |
| *Providencia stuartii* | 33672 |
| *Pseudomonas aeruginosa* | 17933D |
| *Ralstonia pickettii* | 27511 |
| *Salmonella choleraesuis* subsp. *choleraesuis* serotpye *Paratyphi* | 9150D |
| *Serratia odorifera* | 33077 |
| *Shigella flexneri* | 12022 |
| *Shigella sonnei* | 9290 |
| *Staphylococcus aureus* | 29247 |
| *Staphylococcus aureus* subsp. *aure* | 35556D |
| *Staphylococcus hominis* | 27844 |
| *Stenotrophomonas maltophilia* | 13637 |
| *Streptococcus pneumoniae* | 33400 |
| *Streptococcus pyogenes* | 19615 |
| *Streptococcus pyogenes* | 12344D |
| *Yersinia enterocolitica* | NA |
| *Yersinia frederiksenii* | 33641 |
| *Yersinia kristensenii* | 33639 |

TABLE 4-continued

List of organisms used to test cross-reactivity
with the real-time chromosomal PCR assay

| Organism | ATCC # |
|---|---|
| *Yersinia pestis* (CO92; PW) | NA |
| *Yersinia pseudotuberculosis* | 6904 |
| *Yersinia ruckeri* | 29473 |

The optimized assay was tested against a cross-reactivity panel of 77 organisms, including 11 *B. anthracis*. All 11 were detected, regardless of plasmid profile, using the chromosomal marker test, while the remaining 66 organisms failed to produce a signal.

In addition, sensitivity and specificity were evaluated by running 45 *B. anthracis* isolates and 62 *Bacillus* species against the optimized assay (these numbers include the original 16 *B. anthracis* and 13 *B. cereus* tested), shown in Table 3. All *B. anthracis* strains were detected as positive and all of the other *Bacillus* species were negative, including BAC1179, providing 100% sensitivity and specificity.

D. Limit of Detection and Assay Efficacy

The limit of detection was established by running 60 samples of Ames DNA at a single concentration with two negative controls. The results are summarized in Table 5 as follows:

TABLE 5

| Organism | Concentration | Tested | Positive | % positive |
|---|---|---|---|---|
| *Bacillus anthracis* AMES | 50 fg | 60 | 60 | 100% |
| *Bacillus anthracis* AMES | 40 fg | 60 | 47 | 78.3% |

The detection limit was established by testing 60 replicates at a single concentration. The lowest concentration that produced at least a sensitivity of 95% (57 out of 60 positive) was considered the limit of detection. Positive results are determined with the R.A.P.I.D. detector software version 2.0.7.

Of the lowest concentration that was positive, at least 57 out of 60 (about 95%) was determined to be the limit of detection. The efficacy of the assay was determined by testing 10 fold serial dilutions in triplicate from 100 pg to 10 fg. The crossing point (CP) of each dilution was determined using the second derivative method in the LightCycler software 3.3 (Roche, Indianapolis, Ind.). Amplification efficacy was calculated based on the slope of the CP versus the concentration of DNA input using $E=10^{(-1/slope)}$. For an assay to produce unambiguous and identical results, the efficacy of an assay should be as close as possible to 2. This number corresponds to a doubling of template after each PCR cycle.

The developed chromosomal assay resulted in positives incorporating as little as 1 fg of DNA in the reaction. However, the limit of detection was determined to be 50 fg because all 60 samples tested simultaneously at this concentration were detected. At 40 fg only 47 out of 60 samples were detected. Furthermore, an efficacy value of 1.896 was determined and these results are depicted in FIG. 2.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. An isolated nucleic acid molecule consisting of:
   (a) 22 or more consecutive nucleotides of the sequence set forth in SEQ ID NO:1 or its complement;
   (b) 30 or more consecutive nucleotides of the sequence set forth in SEQ ID NO:1 or its complement;
   (c) 40 or more consecutive nucleotides of the sequence set forth in SEQ ID NO:1 or its complement;
   (d) 50 or more consecutive nucleotides of the sequence set forth in SEQ ID NO:1 or its complement;
   (e) 60 or more consecutive nucleotides of the sequence set forth in SEQ ID NO:1 or its complement;
   (f) 70 or more consecutive nucleotides of the sequence set forth in SEQ ID NO:1 or its complement;
   (g) 80 or more consecutive nucleotides of the sequence set forth in SEQ ID NO:1 or its complement;
   (h) 90 or more consecutive nucleotides of the sequence set forth in SEQ ID NO:1 or its complement;
   (i) 100 or more consecutive nucleotides of the sequence set forth in SEQ ID NO:1 or its complement;
   (j) the sequence set forth in SEQ ID NO:1 or its complement.

2. A probe consisting of the isolated nucleic acid molecule of claim 1 and a label.

3. A probe consisting of the isolated nucleic acid molecule of claim 1, a reporter molecule, and a quencher molecule.

4. The probe of claim 3, wherein the reporter molecule produces a signal upon the separation of the reporter molecule and the quencher molecule.

5. The probe of claim 3, wherein the quencher molecule is capable of quenching the signal of the reporter molecule.

6. The probe of claim 3, wherein the reporter molecule is a fluorophore.

7. The probe of claim 6, wherein the fluorophore is FAM, ROX, Texas Red, TET, TAMRA, JOE, HEX, CAL Red, or VIC.

8. The probe of claim 3, wherein the probe is capable of being cleaved by a protein thereby separating the reporter molecule from the quencher molecule.

9. The probe of claim 8, wherein the protein is Taq polymerase.

10. An assay which comprises contacting the probe of claim 2 with a target nucleic acid molecule.

11. The assay of claim 10, wherein the assay is a nucleic acid hybridization assay.

12. The assay of claim 10, wherein the assay is a TaqMan® based assay.

13. The assay of claim 11, further comprising conducting PCR amplification.

14. The assay of claim 13, further comprising detecting the presence or measuring the amount of the probe and detecting the presence or measuring the amount of the target nucleic acid molecule.

15. The assay of claim 14, wherein the absence of the target nucleic acid molecule and the absence of the probe indicate a true negative result for the target nucleic acid molecule.

16. The assay of claim 14, wherein the absence of the target nucleic acid molecule and the presence of the probe indicate a false negative result for the target nucleic acid molecule.

17. A kit for a probe-based nucleic acid assay comprising the isolated nucleic acid molecule of claim 1 packaged with instructions for use.

18. The kit of claim 17, wherein the isolated nucleic acid molecule contains a label.

19. The kit of claim 17, wherein the label is a reporter molecule and a quencher molecule.

20. The kit of claim 17, wherein the probe-based nucleic acid assay is for the detection of an organism.

21. The kit of claim 20, wherein the organism belongs to *Bacillus*.

22. The kit of claim 21, wherein the organism is *Bacillus anthracis*.

23. The kit of claim 19, further comprising reagents or components for detecting the presence of a nucleic acid molecule belonging to the organism.

* * * * *